(12) United States Patent
Mochizuki et al.

(10) Patent No.: US 12,285,500 B2
(45) Date of Patent: Apr. 29, 2025

(54) HYDROGEL PARTICLE AND METHOD FOR PRODUCING SAME, CELL OR CELL STRUCTURE EACH ENCLOSING HYDROGEL PARTICLE THEREIN, METHOD FOR EVALUATING ACTIVITY OF CELL USING HYDROGEL PARTICLE, AND USE OF HYDROGEL PARTICLE AS SUSTAINED RELEASE PREPARATION

(71) Applicants: Konica Minolta, Inc., Tokyo (JP); Yasuhiko Tabata, Kyoto (JP)

(72) Inventors: Makoto Mochizuki, Tokyo (JP); Chie Inui, Tokyo (JP); Natsumi Hirayama, Kyoto (JP); Akihiro Maezawa, Tokyo (JP); Yasuhiko Tabata, Kyoto (JP)

(73) Assignees: KONICA MINOLTA, INC., Tokyo (JP); Yasuhiko Tabata, Kyoto (JP)

( * ) Notice: Subject to any disclaimer, the term of this patent is extended or adjusted under 35 U.S.C. 154(b) by 876 days.

(21) Appl. No.: 16/761,138

(22) PCT Filed: Nov. 5, 2018

(86) PCT No.: PCT/JP2018/041035
§ 371 (c)(1),
(2) Date: May 1, 2020

(87) PCT Pub. No.: WO2019/088292
PCT Pub. Date: May 9, 2019

(65) Prior Publication Data
US 2020/0338218 A1 Oct. 29, 2020

(30) Foreign Application Priority Data
Nov. 6, 2017 (JP) ................. 2017-213707

(51) Int. Cl.
| | |
|---|---|
| *A61K 9/14* | (2006.01) |
| *A61B 5/055* | (2006.01) |
| *A61K 47/02* | (2006.01) |
| *A61K 47/42* | (2017.01) |
| *A61K 49/18* | (2006.01) |
| *A61L 27/52* | (2006.01) |
| *C08J 3/075* | (2006.01) |
| *C08L 101/14* | (2006.01) |

(52) U.S. Cl.
CPC ............ *A61K 49/18* (2013.01); *A61B 5/055* (2013.01); *A61K 9/14* (2013.01); *A61K 47/02* (2013.01); *A61K 47/42* (2013.01); *A61L 27/52* (2013.01); *C08J 3/075* (2013.01); *C08L 101/14* (2013.01)

(58) Field of Classification Search
CPC . A61K 9/14; A61K 9/141; A61K 9/16; A61K 9/143; A61K 9/1605; A61K 9/167; A61K 9/1682; A61K 9/148; A61K 9/145
See application file for complete search history.

(56) References Cited

U.S. PATENT DOCUMENTS

| | | | | |
|---|---|---|---|---|
| 5,427,767 A | * | 6/1995 | Kresse ............... | A61K 49/1863 424/9.322 |
| 2009/0269404 A1 | * | 10/2009 | Ishiguro ............ | A61K 38/1825 514/774 |
| 2012/0213708 A1 | * | 8/2012 | Anderson ............... | A61L 27/52 424/9.2 |
| 2015/0217024 A1 | | 8/2015 | Wang et al. | |
| 2016/0121025 A1 | * | 5/2016 | Yamashita .......... | C12N 5/0657 424/423 |
| 2016/0166504 A1 | * | 6/2016 | Jarrett ..................... | A61K 9/50 424/490 |

FOREIGN PATENT DOCUMENTS

| | | | | |
|---|---|---|---|---|
| CA | 2166705 C | * | 11/2004 | ......... G01N 33/5434 |
| EP | 3395829 A1 | * | 10/2018 | ............ A61K 47/42 |
| JP | 2008-150596 A | | 7/2008 | |
| JP | 2008-214324 A | | 9/2008 | |
| JP | 2010-208979 A | | 9/2010 | |
| JP | 2006-273740 A | | 3/2011 | |
| WO | 2007/111232 A1 | | 10/2007 | |
| WO | 2008/016163 A1 | | 2/2008 | |

(Continued)

OTHER PUBLICATIONS

EPO, Extended European Search Report for the corresponding European Patent Application No. 18872518.8, dated Nov. 16, 2020.
PCT, International Search Report for the corresponding application No. PCT/JP2018/041035, dated Dec. 18, 2018, with English translation (4 pages).
Tomitaka, A., et al., "Preparation of Biodegradable Iron Oxide Nanoparticles with Gelatin for Magnetic Resonance Imaging," Inflammation and Regeneration, 2014, pp. 45-55, vol. 34, No. 1.

(Continued)

*Primary Examiner* — Micah Paul Young
(74) *Attorney, Agent, or Firm* — LUCAS & MERCANTI, LLP

(57) ABSTRACT

The present invention addresses the problem of providing: a hydrogel particle which can be taken into a cell by the action of the cell and can control the release of a magnetic particle enclosed therein into the cell so as to retain the magnetic particle in the cell for a long period; a method for producing the hydrogel particle; a cell or a cell structure each enclosing the hydrogel particle therein; and a method for evaluating the activity of a cell using the hydrogel particle. The present invention solves the problem by a hydrogel particle including: a domain which is composed of a first hydrogel; a matrix which encloses the domain and is composed of a second hydrogel having a different crosslinking degree or composition from that of the first hydrogel; and a magnetic particle which is supported by at least the first hydrogel.

22 Claims, No Drawings

(56) References Cited

FOREIGN PATENT DOCUMENTS

WO 2017/110745 A1 6/2017
WO 2017/110746 A1 6/2017

OTHER PUBLICATIONS

PCT, English translation of Written Opinion of the International Searching Authority for the corresponding application No. PCT/JP2018/041035, dated Dec. 18, 2018.
Office Action dated Jul. 19, 2022, for the corresponding Japanese Patent Application No. 2019-550517, and English translation.

* cited by examiner

HYDROGEL PARTICLE AND METHOD FOR PRODUCING SAME, CELL OR CELL STRUCTURE EACH ENCLOSING HYDROGEL PARTICLE THEREIN, METHOD FOR EVALUATING ACTIVITY OF CELL USING HYDROGEL PARTICLE, AND USE OF HYDROGEL PARTICLE AS SUSTAINED RELEASE PREPARATION

CROSS REFERENCE TO RELATED APPLICATION

This Application is a 371 of PCT/JP2018/041035 filed on Nov. 5, 2018 which, in turn, claimed the priority of Japanese Patent Application No. 2017-213707 filed on Nov. 6, 2017, both applications are incorporated herein by reference.

TECHNICAL FIELD

The present invention relates to a hydrogel particle and a method for producing the hydrogel particle, a cell or a cell structure containing the hydrogel particle, a method for evaluating cell activity by use of the hydrogel particle, and use of the hydrogel particle as a sustained-release formulation.

BACKGROUND ART

There has been increasing demand for a technique for directly introducing a reagent or the like into living cells. For example, a contrast agent can be introduced into living cells, thereby allowing for non-destructive examination of cell activity. Cells into which a contrast agent is introduced can be transplanted into a patient, thereby allowing whether or not the cells transplanted are colonized to be externally observed in a minimally invasive manner, without any re-incision of a transplantation site.

Examples of a technique for introducing a contrast agent into living cells include a liposome encapsulating an MRI contrast agent such as a magnetic material nanoparticle. For example, PTL 1 discloses a liposome containing magnetic microparticles, to which an anti-HMW-MAA antibody is bound. PTL 2 discloses a liposome in which a micelle including a block copolymer and a compound are enclosed. The liposome is for use in DDS (Drug-Delivery-System).

Furthermore, PTL 3 discloses an MRI contrast agent in which a magnetic material nanoparticle is covered with a sugar chain, in order to enhance cellular integration properties of such an MRI contrast agent. NPL 1 describes an iron oxide nanoparticle covered with gelatin.

CITATION LIST

Patent Literatures

PTL 1: Japanese Patent Application Laid-Open No. 2006-273740
PTL 2: Japanese Patent Application Laid-Open No. 2008-214324
PTL 3: Japanese Patent Application Laid-Open No. 2010-208979

Non Patent Literature

NPTL 1 Tomitaka, A. et al. "Preparation of biodegradable iron oxide nanoparticles with gelatin for magnetic resonance imaging" Inflammation and Regeneration, 2014; Vol. 34, No. 1, pp. 45-55

SUMMARY OF INVENTION

Technical Problem

The liposomes as described in PTLs 1 and 2 are not sufficient in biological compatibility and are easily degraded by cells, and thus have a difficulty in allowing release of a substance contained to be controlled. On the other hand, a sugar particle as described in PTL 3 is favorable in biological compatibility. The solubility of the sugar chain, however, is difficult to control and thus release of an encapsulated substance is difficult to control.

A particle with gelatin, as described in NPL 1, can also allow for incorporation into cells by cells' own action. According to the findings of the present inventors, however, a particle having no interior domain or the like and formed of one gelatin is also demanded to achieve maintaining of an encapsulated substance over a longer period of time.

Accordingly, even in a case where a particle including a liposome, a sugar particle, and one gelatin is used to introduce a substance such as a contrast agent into living cells, the total amount of such a substance contained is released in a short period and thus the substance concentration in the cells is expected to be rapidly increased. Such a substance rapidly increased in the cells is discharged out of the cells by cell exocytosis, and thus the substance concentration in the cells is difficult to maintain for a long period even in a case where a large amount of such a substance is contained in the particle.

The present invention has been made in view of the above problems, and an object thereof is to provide a hydrogel particle that can be incorporated by cells' own action and controlled in release of a magnetic material particle encapsulated to thereby allow the magnetic material particle to be maintained in cells for a long period, a cell or a cell structure containing such a hydrogel particle, and a method for evaluating cell activity by use of such a hydrogel particle.

Solution to Problem

The object of the present invention is achieved by the following means.

[1] A hydrogel particle, comprising:
 a domain formed of a first hydrogel;
 a matrix encapsulating the domain and formed of a second hydrogel different in degree of crosslinking or composition from the first hydrogel; and
 a magnetic material particle supported on at least the first hydrogel.

[2] The hydrogel particle according to [1], wherein the magnetic material particle is supported on the first hydrogel and the second hydrogel.

[3] The hydrogel particle according to [1] or [2], wherein the hydrogel particle has an average particle size of 30 nm or more and 2000 nm or less.

[4] The hydrogel particle according to any one of [1] to [3], wherein at least one of the first hydrogel and the second hydrogel is gelatin.

[5] The hydrogel particle according to [4], wherein the second hydrogel is gelatin.

[6] The hydrogel particle according to any one of [1] to [5], wherein the first hydrogel is lower in intercellular degradability than the second hydrogel.

[7] The hydrogel particle according to any one of [1] to [6], wherein the magnetic material particles have an average particle size of 2 nm or more and 25 nm or less.

[8] The hydrogel particle according to any one of [1] to [7], wherein the magnetic material particles are $Fe_3O_4$.

[9] The hydrogel particle according to any one of [1] to [8], further comprising at least one drug supported on at least one of the first hydrogel and the second hydrogel.

[10] The hydrogel particle according to [9], wherein the drug is nucleic acid.

[11] The hydrogel particle according to [10], wherein the nucleic acid is siRNA.

[12] The hydrogel particle according to any one of [1] to [11], further comprising at least one additional domain, wherein the additional domain is formed of another hydrogel different in degree of crosslinking or composition from the first hydrogel and the second hydrogel, and at least one member selected from the group consisting of a magnetic material particle and a drug is supported on the another hydrogel.

[13] The hydrogel particle according to any one of [1] to [12], wherein the magnetic material particle, or the magnetic material particle and the drug is/are sustainably released in cells.

[14] The hydrogel particle according to [13], wherein the hydrogel particle comprises at least two drugs, and the at least two drugs are each independently sustainably released in cells.

[15] A method for producing a hydrogel particle, comprising:
mixing a first hydrogel with magnetic material particles, to thereby provide a first slurry comprising the first hydrogel and the magnetic material particles;
heating the first slurry or adding a phase separation inducer to the first slurry, and particulating the first hydrogel comprising the magnetic material particles, to thereby obtain magnetic material particle-containing microparticles;
mixing a second hydrogel different in degree of crosslinking or composition from the first hydrogel with the magnetic material particle-containing microparticles, to thereby provide a second slurry comprising the second hydrogel and the magnetic material particle-containing microparticles; and
heating the second slurry or adding a phase separation inducer to the second slurry, and particulating the second hydrogel comprising the magnetic material particle-containing microparticles.

[16] A hydrogel particle-encapsulating cell, comprising the hydrogel particle according to any one of [1] to [14] in an interior of a cell membrane.

[17] A hydrogel particle-encapsulating cell structure, comprising the hydrogel particle-encapsulating cell according to [16].

[18] The hydrogel particle-encapsulating cell structure according to [17], wherein the hydrogel particle-encapsulating cell structure is at least one member selected from the group consisting of a cell sheet where a plurality of cells are aggregated in the form of a sheet, a spheroid where a plurality of cells are aggregated in the form of a sphere, a cell bead where a cell population is surrounded by a film, and a cell bead where a cell adheres to a surface of a bead.

[19] The hydrogel particle-encapsulating cell structure according to [17] or [18], wherein the hydrogel particle-encapsulating cell structure is formed from a mixture of the hydrogel particle-encapsulating cell according to [16] and a polymer solution.

[20] A method for evaluating cell activity of living cells, comprising:
introducing a hydrogel particle into living cells, the hydrogel particle comprising a domain formed of a first hydrogel, a matrix encapsulating the domain and formed of a second hydrogel different in degree of crosslinking or composition from the first hydrogel, and magnetic material particles supported on at least the first hydrogel;
obtaining an MRI image of the living cells by use of a signal derived from the magnetic material particle; and
evaluating cell activity of the living cells based on the MRI image obtained.

[21] The method according to [20], wherein the hydrogel particle comprises at least one drug supported on at least one of the first hydrogel and the second hydrogel.

[22] Use of a hydrogel particle, comprising:
a domain formed of a first hydrogel;
a matrix encapsulating the domain and formed of a second hydrogel different in degree of crosslinking or composition from the first hydrogel;
magnetic material particles supported on at least the first hydrogel; and
at least one drug supported on at least one of the first hydrogel and the second hydrogel; as a sustained-release formulation.

Advantageous Effects of Invention

The present invention provides a hydrogel particle that can be incorporated by cells' own action and controlled in release of a magnetic material particle contained to thereby allow the magnetic material particle to be maintained in cells for a long period, and a method for producing such a hydrogel particle, a cell or a cell structure containing such a hydrogel particle, as well as a method for evaluating cell activity by use of such a hydrogel particle.

DESCRIPTION OF EMBODIMENTS

The present inventors have made intensive studies about a release behavior of a hydrogel particle containing a magnetic material particle in cells. As a result, the present inventors have found that a hydrogel particle including at least two hydrogels different in degree of crosslinking or composition, in which the particle includes a domain formed of a first hydrogel and a matrix encapsulating the domain and formed of a second hydrogel, and a magnetic material particle is supported on at least the first hydrogel, can be easily incorporated into cells by cells' own action and can be controlled in release of the magnetic material particle to allow the magnetic material particle to be maintained in cells for a long period. The reason is considered as follows.

A hydrogel is a biologically compatible material, and thus a particle including such a hydrogel as a main component is hardly recognized as a foreign substance by cells, and is easily incorporated into cells due to endocytosis or the like. On the other hand, such a hydrogel is easily degraded in cells, and is demanded to achieve maintaining of an encapsulated substance over a long period. While use of a hydrogel having a hardly degradable composition or a hydrogel high in degree of crosslinking, and/or an increase in particle size can elongate the time taken for degradation of a hydrogel particle in cells, it is difficult that a substance encapsulated in a hydrogel particle is maintained over a long period from several days to several weeks.

The present inventors have then produced a particle encapsulating a magnetic material particle by use of first and second hydrogels different in degree of crosslinking or composition. Specifically, a microparticle including a first hydrogel supporting a magnetic material particle has been produced and the microparticle has been covered with a second hydrogel, thereby producing a hydrogel particle including a domain formed of the first hydrogel and a matrix encapsulating the domain and formed of the second hydrogel. The particle produced has been able to be incorporated into cells by cells' own action, like a particle including one hydrogel. It is considered that the hydrogel particle incorporated into cells allows the matrix formed of the second hydrogel to be first degraded and allows the microparticle including the first hydrogel forming the domain to be gradually released to cytoplasm due to such degradation. It is considered that the microparticle including the first hydrogel, released, is then degraded in the cells and the magnetic material particle supported on the first hydrogel is released in the cells. Thus, degradation until the magnetic material particle is released from the hydrogel particle can be performed at multiple stages, thereby allowing a period from introduction of the magnetic material particle into the cells to complete metabolism to be elongated. It is considered that a large amount of the magnetic material particle is prevented from being released in the cells at one time to thereby inhibit the magnetic material particle from being excreted out of the cells due to exocytosis.

Accordingly, use of the hydrogel particle, as described above, enables a large amount of the magnetic material particle to be maintained in the cells for a long period, and enables detection of cells having the hydrogel particle to be continued at high detectability over a long period.

Hereinafter, a representative embodiment of the present invention will be described in detail.

1. Hydrogel Particle

The present embodiment relates to a hydrogel particle including a domain formed of a first hydrogel, a matrix encapsulating the domain and formed of a second hydrogel different in degree of crosslinking or composition from the first hydrogel, and a magnetic material particle supported on at least the first hydrogel. First, each raw material forming such a hydrogel is described.

1-2. Hydrogel

The hydrogels each refer to a material that can form gel with water as a solvent, and typically include a hydrophilic polymer that forms a network structure, and water incorporated in the network structure. The hydrogels included in the hydrogel particle of the present invention may be each a material that is to be hydrolyzed in cells, or degraded by an enzyme or lysosome secreted in cells.

Examples of the hydrogels include polysaccharides such as chitin, chitosan, hyaluronic acid, alginic acid, agarose, carboxymethyl cellulose (CMC), starch, and pectin, proteins such as gelatin, collagen, fibrin, and albumin, polyamino acids such as poly-γ-glutamic acid, poly-L-lysine, and polyarginine, and synthetic polymers such as acrylamide, silicone, polyvinyl alcohol, polyethylene oxide, and polyvinylpyrrolidone.

In particular, polysaccharides, proteins, and polyamino acids are preferable from the viewpoint that incorporation into living cells is facilitated by the cells by themselves to thereby enable the living cells to be inhibited from being damaged in such incorporation. Furthermore, polysaccharides and proteins are more preferable and gelatin is further preferable in terms of ease of incorporation into cells, availability, or production.

The amount of water included in the hydrogel particle is not particularly limited, and is preferably 1 mass % or more and 99 mass % or less, more preferably 10 mass % or more and 90 mass % or less, further preferably 15 mass % or more and 80 mass % or less based on the total mass of the hydrogel particle after a swelling treatment.

Herein, the "hydrogel particle after a swelling treatment" means a hydrogel particle obtained by immersing a dried hydrogel particle in water at 40° C. under an atmospheric pressure for 60 minutes. Herein, the dried hydrogel particle means a hydrogel particle after standing in air at 80° C. for 24 hours.

The gelatin is a protein that includes 300 or more glycine residues among 1000 amino acid residues and includes both alanine and proline, when analyzed by an amino acid analyzer. The gelatin may any gelatin as long as a particle can be formed, and any known gelatin may be used which is obtained by denaturing collagen derived from cattle bone, cattle skin, pig skin, pig tendon, fish scales, and fish meat. Gelatins have previously been used for foods and for medical purposes, and their intake into the body is hardly harmful to the human body. In addition, gelatins disperse and disappear in the living body, and thus have the advantage of no need for removal from the living body. The above gelatin may include any component other than gelatins as long as the gelatin can be incorporated into cells when formed into a particle. Herein, the amount of such any component other than gelatins is preferably within a range so that any harm to the human body is ignorable in the case of intake of such any component into the body. Such any component other than gelatins preferably includes a substance that is not accumulated in the living body and that is easily excreted.

The weight average molecular weight of the gelatin is preferably 1000 or more and 100000 or less from the viewpoint that the hydrogel particle is easily formed. The weight average molecular weight can be, for example, a value measured according to the PAGI Method Ver. 10 (2006).

The gelatin may be crosslinked. Such crosslinking may be crosslinking with a crosslinking agent, or self-crosslinking made without any crosslinking agent.

The crosslinking agent may be, for example, a compound having a plurality of functional groups that each form a chemical bond with a hydroxyl group, a carboxyl group, an amino group, a thiol group, an imidazole group, or the like. Examples of such a crosslinking agent include glutaraldehyde, water-soluble carbodiimides including 1-ethyl-3-(3-dimethylaminopropyl)carbodiimide hydrochloride (EDC), and 1-cyclohexyl-3-(2-morpholinoethyl)carbodiimide-metho-p-toluenesulfonate (CMC), compounds having two or more epoxy groups, including ethylene glycol diglycidyl ether, polyethylene glycol diglycidyl ether, polyglycol polyglycidyl ether, and glycol polyglycidyl ether, and propylene oxide. In particular, glutaraldehyde and EDC are preferable, and glutaraldehyde is more preferable, from the viewpoint of a more enhancement in reactivity.

Examples of the self-crosslinking include crosslinking made by application of heat, or irradiation with electron beam or ultraviolet light.

The hydrogel particle includes at least two hydrogels (first and second hydrogels) different in degree of crosslinking or composition. The first and second hydrogels may be selected from the above hydrogels, and may be any of a combination of hydrogels different in degree of crosslinking and a combination of hydrogels different in composition.

Herein, the difference in composition between hydrogels means, for example, the difference in ratio of functional groups and the like detected by TEM-EDS measurement, namely, the difference in ratio of a S atom, a N atom, an O atom, a C atom, and a H atom. The difference in ratio of a S atom, a N atom, an O atom, a C atom, and the like can be detected by producing a cross-section sample of the hydrogel particle and performing TEM-EDS measurement. In the present invention, the difference in composition between hydrogels is defined as the difference in content of at least one of a S atom, a N atom, an O atom, a C atom, and a H atom forming such a hydrogel, by 2% or more.

The difference in degree of crosslinking between hydrogels means, for example, the difference in density detected by TEM-EELS measurement. The difference in density can be confirmed as the difference in loss spectrum of TEM-EELS. In the present invention, the difference in degree of crosslinking is defined as the difference in signal intensity of any energy band in a loss spectrum of TEM-EELS, by 2% or more.

The combination of hydrogels different in degree of crosslinking or composition is preferably a combination of hydrogels different in degradability in cells. Two or more hydrogels different in degradability in cells are combined, thereby facilitating control of release of an encapsulated substance. Herein, degradability of such a hydrogel in cells can be evaluated by producing a hydrogel particle on which a labeled substance or the like is supported, introducing the particle into cells, and thereafter measuring the speed of degradation of the particle, with the labeled substance used as an indicator.

A specific hydrogel combination can be selected so that an objective release behavior is achieved, based on the intended use of the hydrogel particle, and the type and the amount of the substance (magnetic material particle or drug) to be contained. It is preferable that a hydrogel which is more hardly degraded be used as a first hydrogel forming a domain and a hydrogel which is more easily degraded be used as a second hydrogel forming a matrix, particularly from the viewpoint that release of a substance contained in the hydrogel particle is defined as sustained releaseability. In a case where the hydrogel particle having such a configuration is incorporated into living cells, a matrix formed of the second hydrogel, which is easily degraded, is first degraded from the outside by, for example, an enzyme (collagenase or the like in a case where the hydrogel is gelatin) present in cytoplasm. As a result, a microparticle formed of the first hydrogel, which is a domain more hardly degraded, is released toward cytoplasm in order of presence from the closest to the outside in the matrix, and a microparticle which is a domain is subsequently degraded.

Herein, the hydrogel particle of the present invention may include two or more domains, as described below, and other hydrogel forming such domains is a hydrogel different in degree of crosslinking or composition from the first and second hydrogels, and is preferably one different in degradability in cells.

At least one of the first and second hydrogels is preferably gelatin from the viewpoint of biological compatibility. Furthermore, the second hydrogel forming a matrix, serving as an outer layer of the particle, is more preferably gelatin, and both first and second hydrogels are further preferably gelatin, in order that incorporation of the hydrogel particle by cells' own action is facilitated.

1-2. Magnetic Material Particle

The magnetic material particle for use in the present invention may be a compound that can detect the presence of a magnetic field (amount of magnetization) according to a procedure for detecting a magnetic field, such as MRI, and examples thereof include gadolinium (Gd), and a metal oxide particle having magnetic properties.

Examples of the metal oxide forming the magnetic material particle include iron oxide, nickel oxide, and manganese oxide. Among these metal oxides, iron oxide is preferable, and magnetite ($Fe_3O_4$), maghemite ($\gamma$-$Fe_2O_3$), and a composite where Fe of such a metal oxide is partially replaced with other atom X are preferable. Examples of such other atom X include LI, Mg, Al, SI, Ca, Sc, TI, V, Cr, Mn, Co, Ni, Cu, Zn, Ga, Ge, Zr, Nb, Mo, Cd, In, Sn, Ta, and W. In the present invention, magnetite ($Fe_3O_4$) is particularly preferable because of being low in cytotoxicity and high in magnetic properties.

The magnetic material particle is preferably a particle having an average particle size of 2 nm or more and 25 nm or less. The average particle size, while depending on the composition of the magnetic material particle, is 2 nm or more, thereby causing no immediate dissolution, degradation or excretion by a cell, to thereby enable detection based on a magnetic field (amount of magnetization) to be continued over a long period. The average particle size is 25 nm or less, thereby making metabolism by living cells easy, to thereby less possibly cause the magnetic material particle to remain in cells for a long period to such an extent that the particle has an adverse effect on the cell.

The magnetic material particle may be used singly or in combinations of two or more kinds of such particles different in average particle size and/or composition. Such two or more magnetic material particles, when used, may be used as a mixture thereof or may be supported on separate sites.

The magnetic material particle is preferably included in an amount of 0.05 volume % or more and 50 volume % or less, more preferably in an amount of 1 volume % or more and 20 volume % or less, based on the total volume of the hydrogel particle, from the viewpoints of an enhancement in detection accuracy and an increase in detection period. In a case where such two or more different magnetic material particles are used, the total amount thereof is preferably within the above range.

1-3. Drug

The hydrogel particle may further include a drug. The drug is, for example, a compound having pharmaceutical activity, a compound considered to have pharmaceutical activity, or a nutritional supplement, and can be appropriately selected depending on the application of the hydrogel particle produced. Specific examples of the compound having pharmaceutical activity include an anticancer agent, an antibiotic substance, an antiviral drug, an antibacterial drug, steroid, a nonsteroidal anti-inflammatory drug (NSAID), an immunosuppressive agent, a function-improving agent of organ, and an antioxidant. Specific examples of the nutritional supplement include vitamins such as vitamin A (retinoid), vitamin D3, and a vitamin D3 analog.

The drug also encompasses proteins and nucleic acids. The hydrogel particle of the present invention can be controlled in release of the magnetic material particle and the drug contained, in cells, and can allow the respective amounts of presence of the particle and the drug to be maintained in cells for a long period, and thus is effective for delivery of nucleic acid having pharmaceutical activity (hereinafter, also referred to as "nucleic acid medicine") to a target site and sustained release at the site, and also monitoring of the effects. Examples of the nucleic acid medicine include plasmid, aptamer, antisense nucleic acid, ribozyme, tRNA, snRNA, siRNA, shRNA, ncRNA, and condensed DNA, and siRNA is particularly preferable.

siRNA (small interfering RNA) usually means low molecular weight double-stranded RNA of 21 to 23 base pairs, and is a molecule that "knocks down" a target gene (namely, specifically suppresses gene expression) by a phenomenon called RNA interference (RNAi). Although the effect is evanescent, use of a siRNA expression vector (for example, plasmid) can also stably express siRNA in cells. It is considered that the hydrogel particle of the present invention is used to introduce siRNA into cells, thereby not only enabling sustained release of siRNA into cells to be achieved, but also enabling whether or not cells into which siRNA is introduced are maintained in a tissue for transplantation to be monitored with the magnetic material particle over a long period.

The drug may be used singly or in combinations of different two or more kinds of such drugs. Such two or more drugs, when used, may be used as a mixture thereof or may be supported on separate sites (matrix and domain).

The content of the drug in the hydrogel particle is not particularly limited, and the drug is preferably included in an amount of 0.0001 volume % or more and 30 volume % or less, more preferably in an amount of 0.05 volume % or more and 5 volume % or less, based on the total volume of the hydrogel particle. In a case where such two or more drugs are used, the total amount thereof is preferably within the above range.

In a case where the drug is supported on both the matrix and the domain, there is not particularly limited as long as the total of the content of the drug in the matrix and the content of the drug in the domain is within the above range. The content of the drug in the matrix is usually 0.00005 volume % or more and 20 volume % or less and the content of the drug in the domain is preferably 0.00005 volume % or more and 20 volume % or less, based on the total volume of the hydrogel particle.

1-4. Structure of Hydrogel Particle

The average particle size of the hydrogel particle is preferably 30 nm or more and 2000 nm or less, more preferably 40 nm or more and 500 nm or less, further preferably 50 nm or more and 200 nm or less from the viewpoint that incorporation into living cells is facilitated by the cells by themselves to thereby inhibit such living cells from being damaged in such incorporation.

A hydrogel particle having an average particle size of 2000 nm or less is easily incorporated into living cells by cells' own action. The reason for this is considered because a biodegradable particle having a particle size of 5.0 µm or less is hardly recognized as a foreign substance by living cells and is easily incorporated into cells due to a mechanism such as endocytosis. On the other hand, a hydrogel particle having an average particle size of 30 nm or more is easily increased in release period of the magnetic material particle (and drug). In particular, the average particle size of the hydrogel particle is 30 nm or more and 2000 nm or less, thereby not only enabling handling properties of the hydrogel particle to be improved, to result in an increase in the amount of the magnetic material particle received, but also enabling incorporation into living cells by cells' own action to be easily made.

The aspect ratio of the dried hydrogel particle is preferably 1.0 or more and 1.4 or less. In a case where the aspect ratio is 1.4 or less, it is considered that the hydrogel particle easily maintains a shape closer to a spherical shape throughout before and after a swelling treatment to thereby allow the hydrogel particle and cells to be contacted in a solution including the hydrogel particle and the cells on a contact surface more uniform in shape and size, thereby hardly causing the difference in ease of incorporation of the hydrogel particle. Thus, it is considered that the hydrogel particle having the aspect ratio is more easily controlled in the amount of the hydrogel particle incorporated into cells and the amount of the cells that incorporate the hydrogel particle. The aspect ratio of the hydrogel particle can be a value determined by dividing a longer diameter of the hydrogel particle by a shorter diameter of the hydrogel particle.

Herein, the average particle size, longer diameter and shorter diameter of the hydrogel particle mean the particle size, longer diameter and shorter diameter of the dried hydrogel particle after standing in air at 80° C. for 24 hours, respectively.

The shorter diameter and the longer diameter of the hydrogel particle can be each value obtained by analysis of an image taken by a scanning electron microscope (SEM). The particle size of the hydrogel particle can be a value obtained by weighted average of the longer diameter and the shorter diameter of the hydrogel particle. In a case where the hydrogel particle is an aggregate, the longer diameter, the shorter diameter, the particle size, and the aspect ratio of the hydrogel particle can be values obtained by respective weighted averages of the longer diameter, the shorter diameter, the particle size, and the aspect ratio with respect to a plurality of such hydrogel particles (for example, 20 hydrogel particles) arbitrarily selected from the aggregate.

The hydrogel particle contains at least one domain. The number of such domains is not particularly limited, and the number of such domains is, preferably 3 or more and 10000 or less, more preferably 5 or more and 5000 or less in terms of the number of such domains per hydrogel particle in order that sustained release of the magnetic material particle included in such domains is achieved.

The average particle size of the domain in the hydrogel particle is preferably 10 nm or more and 1000 nm or less, more preferably 15 nm or more and 50 nm or less, further preferably 20 nm or more and 50 nm or less from the viewpoint of an increase in the amount of the magnetic material particle (and drug) received. In a case where the average particle size of the domain is 10 nm or more, the amount of the magnetic material particle (and drug) received and the time taken for degradation are suitable for achieving sustained releaseability. On the other hand, in a case where the average particle size is 1000 nm or less, the hydrogel particle can contain a proper number of such domains Herein, the domain size and the number of such domains can be confirmed according to the following methods. A section of the hydrogel particle is observed by TEM-EDS or TEM-EELS, and an element mapping or a loss spectrum is obtained. The domain size can be confirmed by performing mapping at any locations different in peak position in the resulting map or spectrum. The number of such domains can be obtained by determining the area corresponding to the domain per unit area of the section of the hydrogel particle, by TEM-EDS or TEM-EELS observation, and performing calculation under the assumption that the domain is uniformly filled at the volume corresponding to the particle size of the hydrogel particle.

In the hydrogel particle of the present invention, the magnetic material particle is supported on at least the first hydrogel. The "supported" means that a substance is immobilized by the hydrogel or a substance is surrounded by the hydrogel.

The magnetic material particle is included in the first hydrogel, namely, the domain, thereby not causing any release of the total amount of the hydrogel particle immediately after the start of degradation thereof. Accordingly, release of the magnetic material particle can be controlled by modulating the types of the first and second hydrogels, and the respective average particle sizes of the hydrogel particle and the domain. For example, the hydrogel particle where the magnetic material particle is supported on only the first hydrogel allows a matrix including the second hydrogel to serve as a shell, to thereby allow the magnetic material particle to be maintained in cells for a long period (namely, the period until complete metabolism of the magnetic material particle is elongated).

The magnetic material particle can also be supported on both the first and second hydrogels. Such a hydrogel particle, where a magnetic material particle to be easily released from the second hydrogel and a magnetic material particle to be later released from the first hydrogel are present, thus allows release of the magnetic material particles to be sustained releaseability. In such a case, it is considered that the concentration of the magnetic material particle in cells is not increased at one time even by supporting of a large amount of the magnetic material particle on the hydrogel particle and thus excretion of the magnetic material particle out of the cells due to exocytosis is suppressed.

Sustained release of the magnetic material particle may be continuous sustained release that imparts release of the magnetic material particle in small portions at short time intervals or gradual sustained release that imparts release of a constant amount of the magnetic material particle at spaced periods. A particle that releases the magnetic material particle from the matrix and thereafter releases the magnetic material particle from the domain is easily designed, and thus gradual sustained release at spaced periods is preferable.

In a case where the hydrogel particle of the present invention is incorporated into cells, the magnetic material particle is preferably maintained in the cells for at least one day, more preferably for 3 days or more and 30 days or less. The period where the magnetic material particle is maintained in the cells can be controlled depending on the compositions and the degrees of crosslinking of the first and second hydrogels, the particle size of the hydrogel particle, the domain size, the number of domains, the type and the amount of a magnetic material used, and the like.

In a case where the hydrogel particle further includes a drug, the drug is supported on at least one of the first and second hydrogels.

In a case where the hydrogel particle includes one drug, the total amount of the drug may be supported on the second hydrogel (matrix), or the total amount of the drug may be supported on the first hydrogel (domain) Alternatively, the drug may be supported on the matrix and the domain in a divided manner.

In a case where a hydrogel particle where the drug is supported on only the second hydrogel forming a matrix and the magnetic material particle is supported on the first hydrogel forming a domain allows the composition (for example, iron, iron oxide or iron ion) forming the magnetic material particle to interact with the drug, the influence of such interaction on a drug efficacy can be suppressed. A hydrogel particle where the drug and the magnetic material particle are supported on the first hydrogel forming a domain allows the matrix formed of the second hydrogel to serve as a shell, and thus enables the time until release of the drug in cells to be elongated. Such a configuration is effective for aiming to delay release of the drug from the hydrogel particle, for example, aiming to certainly deliver the drug to a target site. Furthermore, in a case where the drug is supported on both the first hydrogel and the second hydrogel, the drug supported on the second hydrogel is early released and the drug supported on the first hydrogel is later released, and thus release of the drug has sustained releaseability. In such a case, the concentration of the drug in cells can be maintained at around a certain concentration over a long period without being increased at one time.

In a case where the hydrogel particle includes two or more drugs, the two or more drugs may be supported on the same hydrogel or on separate hydrogels. In a case where such two or more drugs are aimed to act at the same time, the drugs are desirably supported on the same hydrogel. On the other hand, in a case where such two or more drugs are aimed to separately act, the drugs are desirably supported on separate hydrogels. For example, a hydrogel particle where a first drug is supported on the second hydrogel and a second drug is supported on the first hydrogel releases the first drug in cells and releases the second drug after a certain period of time. A hydrogel particle where a liver protection agent is used as the first drug and siRNA is used as the second drug can be introduced into a cirrhotic liver cell, as Examples of the present application, thereby allowing the cirrhotic liver to be at least partially alleviated by the liver protection agent and then enabling siRNA to act.

The hydrogel particle may further include at least one additional domain. Such an additional domain is formed of another hydrogel different in degree of crosslinking or composition from the first hydrogel and the second hydrogel, and at least one member selected from a magnetic material particle and a drug is supported on such other hydrogel. Such an additional domain can be provided to thereby design a hydrogel particle exhibiting a more complicated release behavior. For example, two domains different in intercellular degradability can be used to thereby allow for release of the drug at three stages of the matrix, the first domain, and the second domain (namely, additional domain).

Preferable aspects of the hydrogel, the magnetic material particle, the drug, and the like for use in the additional domain are the same as the hydrogel, the magnetic material particle, the drug, and the like described above. The number of hydrogels used is not limited, and third, fourth, and fifth hydrogels can be used to provide a second domain, a third domain, and a fourth domain. The matrix can also be formed of a plurality of hydrogels and thus controlled in speed of degradation thereof.

Sustained release of the drug from the hydrogel particle may be continuous sustained release that imparts release of the drug in small portions at short time intervals or gradual sustained release that imparts release of a constant amount of the drug at spaced periods. For example, a particle can be designed so as to release the drug from the matrix and thereafter release the drug from the domain, thereby allowing for gradual sustained release at spaced periods. In a case where the hydrogel particle includes a plurality of domains different in degree of crosslinking and the same drug is included in each of the domains, the hydrogel particle can also be designed so that the concentration of the drug released is increased according to a lapse of time.

In a case where the hydrogel particle includes at least two such drugs, the at least two drugs are each independently sustainably released in cells. That is, the at least two drugs may be released in the same pattern or in different patterns.

In a case where release of the drug into cells has sustained releaseability, it is preferable that 0.001 mass % or more and 30 mass % or less of the total amount of the drug originally included in the hydrogel particle be released into the cells 1 hour after introduction of the hydrogel particle into the cell, 35 mass % or more and 50 mass % or less of the total amount of the drug originally included in the hydrogel particle be released into the cells 10 hours after the introduction, and 55 mass % or more and 80 mass % or less of the total amount of the drug originally included in the hydrogel particle be released into the cells 48 hours after the introduction.

The release pattern of the drug from the hydrogel particle can be confirmed according to the following method. To 100 mL of phosphate buffered saline (PBS) targeting cytoplasm is loaded 0.5 g of the hydrogel particle containing the drug, and shaken at 37° C. PBS is collected with respect to each lapse of a certain period, the amount of the drug dissolved out here is quantitatively determined, and thus the release pattern of the drug from the hydrogel particle can be evaluated.

The hydrogel particle containing the magnetic material particle and the drug, exhibiting the above release pattern of the drug, can be used as a sustained-release formulation. The hydrogel particle can be used for prophylaxis and/or therapy of various diseases, depending on the type of the drug contained. Furthermore, the magnetic material particle can be present, to thereby allow for monitoring of cells into which the hydrogel particle is introduced, according to a method for evaluating cell activity, described below.

The hydrogel particle containing the magnetic material particle and the drug can also be used as a Drug-Delivery-System (DDS). For example, an increase in particle size of the hydrogel particle and/or use of a matrix or domain having composition imparting relatively low biodegradability can delay release of the drug from the hydrogel particle to thereby perform controlling so that the drug is not released from the hydrogel particle until attainment to a desired organ.

Herein, the hydrogel particle can include the magnetic material particle, or the magnetic material particle and the drug, and the types and the amounts of the magnetic material particle and the drug, and the sites thereof present in the particle can be confirmed according to the following method.

The type of the magnetic material can be confirmed from a diffraction pattern database of a crystal component, by drying the hydrogel particle and performing XRD measurement. The amount of the magnetic material can be confirmed by grinding the hydrogel particle, thereafter suspending the resultant in water, magnetically separating a magnetic material component by use of a strong magnet such as an electromagnet, and evaluating the weight. The type of the drug contained in the hydrogel particle can be confirmed by extracting the drug from the hydrogel particle and using various instrumental analytical methods such as NMR, IR, LC-mass, MALDI-TOF MASS, Raman spectrum, and elemental analysis. The mass of the drug can be confirmed by separating the drug extracted by water, according to any of various chromatographic methods such as GPC and a gel filtration column, and measuring the mass of a component separated.

In a case where the drug contained in the hydrogel particle is a nucleic acid, the nucleic acid can be extracted from the hydrogel particle, and the nucleic acid can be separated from other substances and nucleic acids different in base sequence, according to a nucleic acid separation procedure such as a density gradient centrifugation method or agarose gel electrophoresis. The base sequence and the number of bases (chain length) of the nucleic acid can be determined by PCR sequencing.

2. Method for Producing Hydrogel Particle

The present embodiment relates to a method for producing the hydrogel particle.

The method for producing the hydrogel particle includes first producing a microparticle including a first hydrogel supporting a magnetic material particle, which is to be formed into a domain, and then producing a particle containing the microparticle produced and including a second hydrogel.

The microparticle including a first hydrogel, namely, the microparticle which is to be formed into a domain can be obtained by preparing a slurry including the first hydrogel and the magnetic material particle (and drug), and heating the slurry prepared or adding a phase separation inducer to the slurry prepared, and particulating the first hydrogel comprising the magnetic material particles (and drug), to thereby obtain magnetic material particle (and drug)-containing microparticles. The method can provide a hydrogel particle where the magnetic material particle (and drug) is uniformly dispersed.

In a case where the hydrogel particle includes at least one additional domain, another hydrogel different in degree of crosslinking or composition from the first hydrogel and the second hydrogel can be used to thereby produce a microparticle including such other hydrogel, according to the same method as described above.

Next, the second hydrogel can be used to produce a hydrogel particle including the microparticle which is to be formed into a domain. For example, a slurry including microparticles including the second hydrogel and the first hydrogel (and microparticles including other hydrogel), and, if necessary, the magnetic material particles and/or a drug can be prepared and the thus prepared slurry can be heated or a phase separation inducer can be added to the slurry prepared, thereby allowing a hydrogel including the microparticles (domain) to be formed into a particle. The particle thus obtained is a hydrogel particle that includes a matrix encapsulating a domain including the first hydrogel and the magnetic material particle (and additional domain) and formed of the second hydrogel.

In such particle formation of a hydrogel by addition of a phase separation inducer to the slurry, a hydrogel particle is formed by coacervation of the hydrogel due to addition of the phase separation inducer. The phase separation inducer added to the slurry is not particularly limited as long as the phase separation inducer is a component that enables the hydrogel to be formed into a particle, and examples include organic solvents, in particular, alcohols such as ethanol, 1-propanol, 2-propanol, and 1-butanol, and acetone.

The amount of an auxiliary component to be supported on the hydrogel particle, for example, the magnetic material particle and the drug, depends on the concentration of the auxiliary component before such particle formation of the hydrogel.

The hydrogel particle is preferably low in the contents of an organic solvent and a low molecular weight component derived from such an organic solvent from the viewpoint of a more reduction in toxicity to living cells. For example, the proportion of a component having a molecular weight of 1000 or less in a molecular weight distribution pattern obtained by dissolving the hydrogel particle in an eluent (0.05 M $Na_2HPO_4$+0.05 M $KH_2PO_4$, pH: 6.8) and performing gel permeation chromatography (GPC) with Asahipak GS620 (column length: 500 nm, column diameter: 7.6 mm×2 columns) manufactured by Asahi Kasei Corporation, as a column, in conditions of a column temperature of 50° C. and a flow rate of 1.0 cc/min by use of an ultraviolet absorption spectrophotometer (detection wavelength: 230 nm) is preferably 5% or less.

3. Hydrogel Particle-Encapsulating Cell and Cell Structure

The present embodiment relates to a hydrogel particle-encapsulating cell including a hydrogel particle in the interior of a cell membrane, and a hydrogel particle-encapsulating cell structure including the cell.

3-1. Cell and Cell Structure

The cell according to the present embodiment (hereinafter, simply referred to as "hydrogel particle-encapsulating cell".) is a cell including the hydrogel particle of the present invention, in the interior of a cell membrane.

The "including the hydrogel particle in the interior of a cell membrane" means that the hydrogel particle is confirmed in the interior of a cell membrane, in an image obtained by taking an image of the cell with TEM. Incorporation of the hydrogel particle into the cells can be confirmed about, for example, whether or not the hydrogel particle including the magnetic material particle is incorporated into the cell, according to observation of the magnetic material particle after staining, with a microscope, or imaging with MRI. Alternatively, the hydrogel particle can also be fluorescently labeled in advance and whether or not the hydrogel particle fluorescently labeled is incorporated into the cells can be confirmed with a confocal microscope. The hydrogel particle can be fluorescently labeled by, for example, using, as a substrate, a FITC-hydrogel prepared by mixing equal amounts of a fluorescein isothiocyanate (FITC)-labeled solution (for example, a 10 mM solution of FITC-collagen manufactured by Cosmo Bio Co., Ltd., in acetic acid), 0.4 M sodium chloride, 0.04% (W/V) sodium azide, and 50 mM Tris-hydrochloric acid buffer (pH 7.5) including 10 mM calcium chloride, and thereafter subjecting the resultant to a heating treatment at 60° C. for 30 minutes.

The hydrogel particle to be included in the cell, which supports the magnetic material particle, in particular, the magnetic material particle serving as a contrast agent for MRI, thus can be produced by a method for incorporation by cells' own action, as described below, and thereafter observed with respect to the presence of the magnetic material particle in the cell, thereby allowing cell activity to be non-destructively examined.

A cell capable of including the hydrogel particle in the interior of a cell membrane, here used, can be any of known cells including cells derived from biological samples or specimens extracted from various organs such as bone marrow, heart, lung, liver, kidney, pancreas, spleen, intestinal tract, small intestine, cardiac valve, skin, blood vessel, cornea, eyeball, dura mater, bone, trachea, and auditory ossicle, commercially available established cell line, and stem cells including skin stem cell, epidermal keratinocyte stem cell, retinal stem cell, retinal epithelial stem cell, cartilage stem cell, hair follicle stem cell, muscle stem cell, osteoprogenitor stem cell, adipose progenitor cell, hematopoietic stem cell, nerve stem cell, hepatic stem cell, pancreatic stem cell, ectodermal stem cell, mesodermal stem cell, endodermal stem cell, mesenchymal stem cell, ES cell, and iPS cell, and cells differentiated from such cells.

The hydrogel particle-encapsulating cell can form a cell structure with a plurality of cells collected. The form of such a cell structure is not particularly limited, and examples thereof include a cell sheet as a two-dimensional culture, a spheroid (cell mass) as a three-dimensional culture, a cell bead where a cell population is surrounded by a film, and a cell bead where a cell adheres to the surface of a bead. Other component than the cell included in the cell structure, for example, the film and/or the bead, preferably includes a biologically compatible material. Examples of the biologically compatible material include polymer components such as laminin, proteoglycan, fibrin, matrigel, chitosan gel, polyethylene glycol, gelatin, and alginic acid.

A cell structure having a three-dimensional structure can be formed from a mixture of the hydrogel particle-encapsulating cell and a polymer solution. Specifically, the polymer solution is prepared by using one or more polymer components (laminin, proteoglycan, fibrin, matrigel, chitosan gel, polyethylene glycol, gelatin, alginic acid, and the like), the hydrogel particle-encapsulating cell is embedded therein and here cultured, and thus formed into a sheet-shaped or mass-shaped cultured cell, and such a cultured cell is further integrated to thereby form a larger cell population. The population of the cultured cell, thus formed, can be used as a tissue-like cell structure.

The type of the hydrogel particle-encapsulating cell forming the cell structure is not particularly limited, and, for example, skeletal muscle cell, smooth muscle cell, neurocyte, hepatocyte, cardiomyocyte, keratinocyte, or stem cell such as ES cell or iPS cell can be used. The cell structure may include at least one of the hydrogel particle-encapsulating cell, or may include two or more such hydrogel particle-encapsulating cells, or the hydrogel particle-encapsulating cell and other cell. For example, a hydrogel particle-encapsulating cell for tissue formation and a cell for vascular formation can be used to provide an organ-like three-dimensional cell structure having a blood vessel.

Among such cells, a cell and a cell structure to be transplanted into a patient in cell regeneration medicine, in particular, a stem cell or a cell differentiated from a stem cell can include a hydrogel particle supporting the magnetic material particle, and thus can be observed about whether or not a hydrogel particle-encapsulating cell is colonized in a transplantation site, without reoperation, by observation of the magnetic material particle in the transplantation site after transplantation into the patient. Thus, it is considered that such a cell including the hydrogel particle supporting the magnetic material particle can reduce any physical, mental, financial, and temporal burden on a patient receiving therapy of regeneration medicine and improve quality of life (QOL) of the patient.

3-2. Method for Producing Cell

The hydrogel particle-encapsulating cell can be produced by introducing a hydrogel particle into cells. Examples of the method for introducing a hydrogel particle into cells include a method where a hydrogel particle and a cell are added into a liquid and thus incorporation by cells' own action such as incorporation due to endocytosis is made, and a method where introduction is made by an external operation. Examples of such a method for incorporation by cells' own action include a method where a hydrogel particle and cells are stirred in a liquid, and a method where cells are cultured in a cell culture solution including a hydrogel particle. The hydrogel particle is high in incorporation efficiency by cells by themselves, and thus there is no particular need for any operation that forms a composite with other component in order to accelerate incorporation into the cell. The method including mixing and culturing a hydrogel particle and cells in a liquid is preferable from the viewpoint that deterioration in cell activity is kept to the minimum Examples of the method where introduction is made by an external operation include an electroporation method and a microinjection method. In particular, such a method for incorporation by cells' own action is preferable, and such a method for incorporation into cells with no formation of the composite is more preferable from the viewpoint that cell activity is hardly decreased in introduction of a hydrogel particle.

A cell culture solution can be used as the liquid to which a hydrogel particle and cells are to be added. The cell culture solution that can be used is, for example, a Hanks culture solution and a HEPES culture solution. The cell culture solution may a known buffer or saline, and can be, for example, any of a Hank's balanced salt solution (HBSS), 4-(2-hydroxyethyl)-1-piperazineethanesulfonic acid (HEPES), and other known phosphate buffered saline (PBS).

The temperature of the cell culture solution in the above stirring is preferably 15° C. or more and 50° C. or less, more preferably 35° C. or more and 45° C. or less from the viewpoint that cell activity is increased to allow a hydrogel particle to be easily incorporated into cells by cells' own action.

When the hydrogel particle is introduced into the interior of a cell membrane by cells' own action, for example, a cell culture solution including a hydrogel particle and the cell may be shaken to accelerate such introduction.

4. Method for Evaluating Cell Activity of Cells

The present embodiment relates to a method for evaluating cell activity of living cells, including: introducing a hydrogel particle into living cells; obtaining an MRI image of the living cells by use of a signal derived from a magnetic material particle included in the hydrogel particle; and evaluating cell activity of the cells based on the MRI image obtained.

The hydrogel particle of the present invention exhibits biological compatibility, and thus is incorporated into cells and then completely metabolized with time. The period taken for the complete metabolism depends on the state of the cells. For example, in a case where the cells is a liver cell, the time taken for the complete metabolism of the hydrogel particle is longer in abnormal hepatocytes due to cirrhotic liver than in a normal cell. Accordingly, cell activity of the cells can be evaluated by introducing the hydrogel particle into the cell, using a signal derived from the magnetic material particle to provide an MRI image, and monitoring metabolic activity of the cells based on the resulting MRI image.

It is known that metabolic activity is more increased in the case of cancer cells than in the case of normal cells. Accordingly, not only deterioration in metabolism, but also an abnormal increase in metabolism serves as an indicator with respect to the state of the cells.

In a case where the hydrogel particle further contains a drug, cell activity of the cells can be evaluated to thereby allow the effect of the drug contained, on the cell activity, to be evaluated. For example, in a case where a hydrogel containing a drug is introduced into abnormal cells and the cell activity is enhanced, the drug is considered to have a therapeutic effect. In a case where a hydrogel containing a drug is introduced into normal cells and the cell activity is deteriorated, the drug is considered to have an undesirable adverse effect.

Herein, such a drug to be evaluated with cell activity as an indicator can also be separately added to cells into which the hydrogel particle is introduced, without being contained in the hydrogel particle.

In a case where a hydrogel particle including a drug is introduced into cells and the cells are transplanted into a living body, whether or not the cells transplanted are colonized can be determined by evaluation of cell activity. Specifically, the activity is considered to be enhanced when the state of the cells is improved by the drug released from the hydrogel particle, and thus, if the activity of the cells transplanted is enhanced, the cells encapsulating the hydrogel particle can be thus considered to be colonized at a site for transplantation.

An apparatus for obtaining an MRI image by use of a signal from the magnetic material particle is not particularly limited, and a common MRI apparatus can be used.

EXAMPLES

Hereinafter, specific Examples of the present invention will be described. It is noted that the scope of the present invention is not construed as being limited by these Examples.

Examples 1 to 21: Production of Magnetic Material Particle-Encapsulating Hydrogel Particle 1-1. Raw Materials The following raw materials were used for production of each magnetic material particle-encapsulating hydrogel particle.

(Hydrogel)
  Porcine skin gelatin: porcine skin water-soluble gelatin (acid) (manufactured by Nippi. Inc.)
  Fishskin gelatin: fishskin gelatin subjected to acid treatment (manufactured by Nippi. Inc.)
  Silicone: polydimethylsiloxane (manufactured by Wako Pure Chemicals Industries, Ltd.)
  PVA (polyvinyl alcohol): PVA-617 (manufactured by Kuraray Co., Ltd.)

(Magnetic Material Particle)
  $Fe_3O_4$ nanoparticle (1 nm): item number 790508 (manufactured by Sigma-Aldrich Co., LLC) was classified by centrifuge to adjust slurry having a center particle size of 1 nm.
  $Fe_3O_4$ nanoparticle (5 nm): item number 790508 (manufactured by Sigma-Aldrich Co., LLC)
  $Fe_3O_4$ nanoparticle (10 nm): item number 747254 (manufactured by Sigma-Aldrich Co., LLC)
  $Fe_3O_4$ nanoparticle (20 nm): item number 900088 (manufactured by Sigma-Aldrich Co., LLC)
  $Fe_3O_4$ nanoparticle (30 nm): item number 900062 (manufactured by Sigma-Aldrich Co., LLC)
  NiO nanoparticle (10 nm): manufactured by Corefront Corporation
  $Mn_3O_4$ nanoparticle (10 nm): manufactured by IOX Co., Ltd.

(Drug)
  siRNA: ND-L02-s0201 (manufactured by Nitto Denko Corporation/Quark Pharmaceuticals)
  Liver protection drug: glycyrrhizin (Crosslinking Agent)
  Glutaraldehyde: manufactured by Wako Pure Chemicals Industries, Ltd.
  Glycine: manufactured by Wako Pure Chemicals Industries, Ltd.
  Tetraethyl orthosilicate (TEOS): manufactured by Wako Pure Chemicals Industries, Ltd.

1-2. Production of Gel Domain

The hydrogel, the magnetic material particle, and a solvent were mixed so that each composition shown in Table 1 below was achieved, and were dispersed by an ultrasonic dispersing machine for 30 minutes. In a case where a gel domain including the drug was produced, 20 nmol of the drug described in Table 1 was subsequently loaded, and stirred for 10 minutes. To the resulting mixture was added 2 mL of 1 M NaOH, a crosslinking agent described in Table 1 was subsequently added, and the resultant was stirred for 5 minutes. In the case of the designation "Glutaraldehyde/glycine cap" in the Table, 0.5 g of glutaraldehyde was added and stirred for 5 minutes, and thereafter 50 mL of 0.1 M glycine was further added and stirred for 1 hour, thereby capping an aldehyde group.

Next, 250 mL in total of each reprecipitation solvent described in Table 1 was dropped with a syringe having an inner diameter of 100 μm, thereby providing a magnetic material particle singly, or a microparticle containing the magnetic material particle and the drug, which was to be formed into a gel domain

TABLE 1

| No. | First hydrogel (4 g) | Magnetic material particle (particle size) (0.8 g) | Solvent (200 mL) | Drug (20 nmol) | Crosslinking agent (0.5 g) | Reprecipitation solvent (250 ml) |
|---|---|---|---|---|---|---|
| 1 | Porcine skin gelatin | $Fe_3O_4$ (10 nm) | Water | — | Glutaraldehyde/glycine cap | Acetone/water = 9/1 |
| 2 | Porcine skin gelatin | $Fe_3O_4$ (10 nm) | Water | — | Glutaraldehyde/glycine cap | Acetone/water = 9/1 |
| 3 | Porcine skin gelatin | $Fe_3O_4$ (10 nm) | Water | — | Glutaraldehyde/glycine cap | Acetone/water = 9/1 |
| 4 | Porcine skin gelatin | $Fe_3O_4$ (10 nm) | Water | — | Glutaraldehyde/glycine cap | Acetone/water = 9/1 |
| 5 | Porcine skin gelatin | $Fe_3O_4$ (10 nm) | Water | siRNA | Glutaraldehyde/glycine cap | Acetone/water = 9/1 |
| 6 | Porcine skin gelatin | $Fe_3O_4$ (10 nm) | Water | siRNA | Glutaraldehyde/glycine cap | Acetone/water = 9/1 |
| 7 | Porcine skin gelatin | $Fe_3O_4$ (10 nm) | Water | siRNA | Glutaraldehyde/glycine cap | Acetone/water = 9/1 |
| 8 | Porcine skin gelatin | $Fe_3O_4$ (10 nm) | Water | siRNA | Glutaraldehyde/glycine cap | Acetone/water = 9/1 |
| 9 | Porcine skin gelatin | $Fe_3O_4$ (10 nm) | Water | siRNA | Glutaraldehyde/glycine cap | Acetone/water = 9/1 |
| 10 | Porcine skin gelatin | $Fe_3O_4$ (10 nm) | Water | siRNA | Glutaraldehyde/glycine cap | Acetone/water = 9/1 |
| 11 | Silicone | $Fe_3O_4$ (10 nm) | Water | siRNA | TEOS | Acetone |
| 12 | Porcine skin gelatin | NiO (10 nm) | Water | siRNA | Glutaraldehyde/glycine cap | Acetone/water = 9/1 |
| 13 | Porcine skin gelatin | $Mn_3O_4$ (10 nm) | Water | siRNA | Glutaraldehyde/glycine cap | Acetone/water = 9/1 |
| 14 | Porcine skin gelatin | $Fe_3O_4$ (10 nm) | Water | siRNA | Glutaraldehyde/glycine cap | Acetone |
| 15 | Porcine skin gelatin | $Fe_3O_4$ (10 nm) | Water | siRNA | Glutaraldehyde/glycine cap | Acetone/water = 8/2 |
| 16 | Porcine skin gelatin | $Fe_3O_4$ (10 nm) | Water | siRNA | Glutaraldehyde/glycine cap | Acetone/water = 7/3 |
| 17 | Porcine skin gelatin | $Fe_3O_4$ (10 nm) | Water | siRNA | Glutaraldehyde/glycine cap | Acetone/water = 6/4 |
| 18 | Porcine skin gelatin | $Fe_3O_4$ (1 nm) | Water | siRNA | Glutaraldehyde/glycine cap | Acetone/water = 9/1 |
| 19 | Porcine skin gelatin | $Fe_3O_4$ (5 nm) | Water | siRNA | Glutaraldehyde/glycine cap | Acetone/water = 9/1 |
| 20 | Porcine skin gelatin | $Fe_3O_4$ (20 nm) | Water | siRNA | Glutaraldehyde/glycine cap | Acetone/water = 9/1 |
| 21 | Porcine skin gelatin | $Fe_3O_4$ (30 nm) | Water | siRNA | Glutaraldehyde/glycine cap | Acetone/water = 9/1 |

1-3. Production of Particle Including Gel Domain and Gel Matrix

The hydrogel and a solvent, and, if desired, the magnetic material particle were mixed so that each composition shown in Table 2 below was achieved, and were dispersed by an ultrasonic dispersing machine for 30 minutes. Next, 4 g of the microparticle first produced, which was to be formed into a gel domain, or 4 g of the microparticle and 20 nmol of the drug described in Table 2 were loaded, and stirred for 10 minutes. To the resulting mixture was added 2 μL of 1 M NaOH, the crosslinking agent described in Table 2 was subsequently added, and stirred for 5 minutes. Next, 250 mL in total of each reprecipitation solvent described in Table 2 was dropped with a syringe having an inner diameter of 100 μm, thereby providing a hydrogel particle containing a gel domain.

The above method provided a hydrogel particle containing a gel domain having each composition shown in Table 1, in each gel matrix shown in Table 2.

TABLE 2

| No. | Second hydrogel (4 g) | Magnetic material particle (particle size) (0.8 g) | Solvent (200 ml) | Drug (20 nmol) | Crosslinking agent (amount) | Reprecipitation solvent (250 ml) |
|---|---|---|---|---|---|---|
| 1 | Porcine skin gelatin | — | Water | — | Glutaraldehyde (0.1 g)/glycine cap | Acetone/water = 9/1 |
| 2 | Fishskin gelatin | — | Water | — | Glutaraldehyde (0.5 g)/glycine cap | Acetone/water = 9/1 |
| 3 | Porcine skin gelatin | $Fe_3O_4$(10 nm) | Water | — | Glutaraldehyde (0.1 g)/glycine cap | Acetone/water = 9/1 |
| 4 | Fishskin gelatin | $Fe_3O_4$(10 nm) | Water | — | Glutaraldehyde (0.5 g)/glycine cap | Acetone/water = 9/1 |
| 5 | Porcine skin gelatin | — | Water | — | Glutaraldehyde (0.1 g)/glycine cap | Acetone/water = 9/1 |
| 6 | Porcine skin gelatin | $Fe_3O_4$(10 nm) | Water | siRNA | Glutaraldehyde (0.1 g)/glycine cap | Acetone/water = 9/1 |
| 7 | Fishskin gelatin | — | Water | — | Glutaraldehyde (0.5 g)/glycine cap | Acetone/water = 9/1 |
| 8 | Fishskin gelatin | $Fe_3O_4$(10 nm) | Water | siRNA | Glutaraldehyde (0.5 g)/glycine cap | Acetone/water = 9/1 |
| 9 | Porcine skin gelatin | $Fe_3O_4$(10 nm) | Water | Liver protection drug | Glutaraldehyde (0.1 g)/glycine cap | Acetone/water = 9/1 |
| 10 | Fishskin gelatin | $Fe_3O_4$(10 nm) | Water | Liver protection drug | Glutaraldehyde (0.5 g)/glycine cap | Acetone/water = 9/1 |
| 11 | PVA | $Fe_3O_4$(10 nm) | Water | Liver protection drug | — | Acetone/water = 9/1 |
| 12 | Porcine skin gelatin | NiO(10 nm) | Water | Liver protection drug | Glutaraldehyde (0.1 g)/glycine cap | Acetone/water = 9/1 |
| 13 | Porcine skin gelatin | $Mn_3O_4$(10 nm) | Water | Liver protection drug | Glutaraldehyde (0.1 g)/glycine cap | Acetone/water = 9/1 |
| 14 | Porcine skin gelatin | $Fe_3O_4$(10 nm) | Water | Liver protection drug | Glutaraldehyde (0.1 g)/glycine cap | Acetone |
| 15 | Porcine skin gelatin | $Fe_3O_4$(10 nm) | Water | Liver protection drug | Glutaraldehyde (0.1 g)/glycine cap | Acetone/water = 8/2 |
| 16 | Porcine skin gelatin | $Fe_3O_4$(10 nm) | Water | Liver protection drug | Glutaraldehyde (0.1 g)/glycine cap | Acetone/water = 7/3 |
| 17 | Porcine skin gelatin | $Fe_3O_4$(10 nm) | Water | Liver protection drug | Glutaraldehyde (0.1 g)/glycine cap | Acetone/water = 6/4 |
| 18 | Porcine skin gelatin | $Fe_3O_4$(1 nm) | Water | Liver protection drug | Glutaraldehyde (0.1 g)/glycine cap | Acetone/water = 9/1 |
| 19 | Porcine skin gelatin | $Fe_3O_4$(5 nm) | Water | Liver protection drug | Glutaraldehyde (0.1 g)/glycine cap | Acetone/water = 9/1 |
| 20 | Porcine skin gelatin | $Fe_3O_4$(20 nm) | Water | Liver protection drug | Glutaraldehyde (0.1 g)/glycine cap | Acetone/water = 9/1 |
| 21 | Porcine skin gelatin | $Fe_3O_4$(30 nm) | Water | Liver protection drug | Glutaraldehyde (0.1 g)/glycine cap | Acetone/water = 9/1 |

1-4. Average Particle Size

The average particle size of the hydrogel particle produced above was measured according to the following method.

An image of the hydrogel particles was taken by a scanning electron microscope (SEM). The image taken was analyzed with an image analyzing particle size distribution measurement software Mac-View manufactured by Mountech Co., Ltd., the shorter diameter and the longer diameter of each of 20 particles arbitrarily selected were measured, and the average thereof was determined and defined as the average particle size.

The average particle size measured, together with the composition of each hydrogel particle, was described in Table 3 and Table 4.

1-5. Evaluation Criteria

Hydrogel particles 1 to 21 were evaluated according to the following methods (1) to (4), and the results are shown in Table 3 and Table 4.

(1) Long-Term Imaging of Cell Activity

A normal mouse hepatocytes were seeded in a cell culture dish, and cultured in phosphate buffer. Subsequently, hydrogel particles 1 to 21 (100 mg/mL, namely, 500 μL) produced above were each dropped in the cell culture dish, and left to still stand for 24 hours. Thus, such particles were each introduced into the cells by cell endocytosis. Subsequently, any hydrogel particle not introduced into the cells was washed off with phosphate buffer, and the resulting cell was defined as a cell containing each of the particles.

The T2 value was measured 1 hour and 7 days after introduction of each of the particles, with an MRI apparatus (M10, manufactured by Primetech Corporation), and the change in amount of a magnetic material in the cells was evaluated based on the following criteria.

A: the T2 value (1 hour later)/T2 value (7 days later) was 0.4 or more

B: the T2 value (1 hour later)/T2 value (7 days later) was 0.05 or more and less than 0.4

C: the T2 value (1 hour later)/T2 value (7 days later) was less than 0.05

(2) Long-Term Sustained-Release of Drug (2a) Case of siRNA as Drug

A 10-base-pair oligomer complementary to siRNA (ND-L02-s0201) introduced as the drug into each of the particles was prepared, and labeled by a rhodamine dye to thereby provide a fluorescent tag. Subsequently, each of hydrogel particles 1 to 21, containing only the magnetic material particle or the magnetic material particle and the drug, was introduced into normal hepatocytes. Into such hepatocytes, into which each of the hydrogel particles was introduced, was dropped 2 mL of the fluorescent tag diluted with phosphate buffer to 5 μM, and incubated for 2 hours to thereby perform fluorescent labelling of siRNA. Subsequently, such hepatocytes were washed with phosphate buffer, and any unbound fluorescent tag was removed. Thereafter, an operation where washing of such hepatocytes with phosphate buffer was performed once daily was performed for 14 days.

Here, the intensity of fluorescence derived from the fluorescent tag 1 hour and 7 days after introduction of the fluorescent tag into such hepatocytes was measured with a fluorescence plate reader (Spark (trademark) 10 M, manufactured by Tecan Trading AG), and the long-term sustained-releaseability of the drug was evaluated according to the following criteria.

A: the intensity of fluorescence (7 days later)/intensity of fluorescence (1 hour later) was 0.3 or more B: the intensity of fluorescence (7 days later)/intensity of fluorescence (1 hour later) was 0.1 or more and less than 0.3

C: the intensity of fluorescence (7 days later)/intensity of fluorescence (1 hour later) was less than 0.1

(2b) Case of Liver Protection Drug as Drug

Glycyrrhizin synthesized with a raw material including $C^{14}$ as an isotope of carbon was prepared, and a hydrogel particle containing the drug was prepared. Each of hydrogel particles 1 to 21, containing only the magnetic material particle or the magnetic material particle and the drug, was introduced into a normal hepatocyte. Subsequently, an operation where washing of such hepatocytes with phosphate buffer was performed once per day was performed for 14 days.

Here, the signal intensity derived from a carbon isotope $C^{14}$ 1 hour and 7 days after introduction of the hydrogel particle into such hepatocytes was measured with an isotope ratio mass analyzer (253 Plus 10 kV, manufactured by Thermo Fisher Scientific), and the long-term sustained-releaseability of the drug was evaluated according to the following criteria.

A: the signal intensity (7 days later)/signal intensity (1 hour later) was 0.3 or more B: the signal intensity (7 days later)/signal intensity (1 hour later) was 0.1 or more and less than 0.3

C: the signal intensity (7 days later)/signal intensity (1 hour later) was less than 0.1

(2c) Case of a Plurality of Different Drugs Included

In a case where the hydrogel particle included a plurality of different drugs (siRNA and liver protection drug), multi-stage release of the drug was further evaluated as follows.

Measurement of the intensity of fluorescence in (2a) and measurement of the isotope ratio in (2b) were performed every hour, the time at which the amount of release reached the peak was determined with respect to each drug, and multi-stage release evaluation of each drug was performed according to the following criteria.

A: the difference in time of the peak of release between respective drugs was 3 hours or more B: the difference in time of the peak of release between respective drugs was 1 hour or more and less than 3 hours C: the difference in time of the peak of release between respective drugs was less than 1 hour (3) Proportion of Cell into Which Particle was Introduced Each of hydrogel particles 1 to 21 was introduced into cells in the same manner as in (1), whether or not any hydrogel incorporated in the interior of a cell membrane could be confirmed was observed, and the proportion of the cell into which each of the particles was introduced was evaluated according to the following criteria.

(Staining of Cell and Fe)

To cells cultured was added 1 ml of 1% paraformaldehyde, to perform a cell immobilization treatment. Next, 1 ml of a Fe staining solution having the following composition was added to stain Fe. Furthermore, 1 ml of a nuclear staining solution having the following concentration adjusted was added to stain the cell.

(Staining of Cells and NiO or $Mn_3O_4$)

To cells cultured was added 1 ml of 1% paraformaldehyde, to perform a cell immobilization treatment. Next, 1 ml of a Ni/Mn staining solution having the following composition was added to stain Ni or Mn. Furthermore, 1 ml of a nuclear staining solution having the following concentration adjusted was added to stain the cell.

(Composition of Fe Staining Solution)

Equal volumes of the following two liquids were mixed, thereby preparing a Fe staining solution.

20 volume % HCL (5-fold dilution of concentrated hydrochloric acid)

Aqueous 10 mass % $K_4(Fe(CN)_6)$ solution (100 mg/ml)

(Composition of Ni/Mn Staining Solution)

A 100 mg/ml solution of PhenanGreen SK, Diacetate (manufactured by Funakoshi Co., Ltd.) was prepared, and adopted as a staining solution of Ni and Mn.

(Composition of Nuclear Staining Solution)

Five parts by mass of ammonium sulfate and 0.1 parts by mass of Nuclear fast red were mixed with 100 parts by mass of distilled water, thereby preparing a nuclear staining solution.

(Counting of Number of Cells Incorporating Fe)

The cells stained were observed with an optical microscope, and whether or not Fe blue-stained was included in 20 cells arbitrarily selected was evaluated.

A: Incorporation of gelatin into the interior of a cell membrane could be confirmed in 50% or more (10 or more) cells out of the 20 cells B: Incorporation of gelatin into the interior of a cell membrane could be confirmed in 10% or more and less than 50% (2 or more and less than 10) cells out of the 20 cells C: Incorporation of gelatin into the interior of a cell membrane could be confirmed in less than 10% (less than 2) cells out of the 20 cells (Counting of Number of Cells Incorporating Ni or Mn)

The cells stained were observed with an optical microscope, and whether or not Ni or Mn green-stained was included in 20 cells arbitrarily selected was evaluated.

A: Incorporation of gelatin into the interior of a cell membrane could be confirmed in 50% or more (10 or more) cells out of the 20 cells B: Incorporation of gelatin into the interior of a cell membrane could be confirmed in 10% or more and less than 50% (2 or more and less than 10) cells out of the 20 cells C: Incorporation of gelatin into the interior of a cell membrane could be confirmed in less than 10% (less than 2) cells out of the 20 cells (4) Complete Metabolism of Particle in Cell Each of hydrogel particles 1 to 21 was introduced into normal mouse hepatocytes. An operation where washing of such hepatocytes with phosphate buffer was performed once per day was performed for 14 days. Subsequently, the remaining metal element (the amount of Fe, the amount of Ni, or the amount of Mn) derived from the magnetic material was measured with respect to such hepatocytes into which each of the particles was introduced, according to an atomic absorption method. The amount of a metal element (the amount of Fe, the amount of Ni, or the amount of Mn) in any hepatocytes into which no particle was introduced was measured as a control, and the value was subtracted from that of the remaining metal element in such hepatocytes into which each of the particles was introduced, and the amount of the remaining metal element derived from the magnetic material was obtained. The complete metabolism of each of the particles in such hepatocytes was evaluated based on the resulting value, according to the following criteria.

A: the amount of the remaining metal element derived from the magnetic material was less than 1 ng/cell B: the amount of the remaining metal element derived from the magnetic material was 1 ng/cell or more and less than 10 ng/cell C: the amount of the remaining metal element derived from the magnetic material was 10 ng/cell or more Comparative Example 1: Production of Liposome Containing Magnetic Material and Drug To 10 mL of a liposome dispersion (Plain DPPC/CHOL Liposomes, manufactured by Funakoshi Co., Ltd.) were added 1 mL of a 10 w % magnetic material ($Fe_3O_4$) dispersion and 50 nmol of siRNA, and stirred at room temperature for 2 hours, thereby providing a liposome containing the magnetic material and the drug. The average particle size of the resulting liposome was measured in the same manner as in 1-4, and further evaluated in the same manner as in 1-5.

Comparative Example 2: Production of Sugar Particle Containing Magnetic Material and Drug To 10 mL of an aqueous 10 w % sucrose solution were added 1 mL of a 10 w % magnetic material ($Fe_3O_4$) dispersion and 50 nmol of siRNA, and stirred at room temperature for 2 hours, thereby providing a mixture. Subsequently, the resulting mixture was formed into a microparticle by a freeze-grinding machine (JFC-2000 manufactured by Japan Analytical Industry Co., Ltd.), thereby providing a sugar particle containing the magnetic material and the drug. The average particle size of the resulting sugar particle was measured in the same manner as in 1-4, and further evaluated in the same manner as in 1-5.

The characteristics of the particles produced in Comparative Examples 1 and 2, together with the evaluation results of such particles, were shown in Table 5.

TABLE 3

| | Gel domain | | | Gel matrix | | | Evaluation results | | | | |
|---|---|---|---|---|---|---|---|---|---|---|---|
| Example | First hydrogel (degree of crosslinking) | Magnetic material particle (particle size) | Drug | Second hydrogel (degree of crosslinking) | Magnetic material particle (particle size) | Drug | Average particle size of hydrogel particle | Long-term imaging of cell activity | Long-term sustained-release/time lag release, of drug | Proportion of cells into which particle is introduced | Complete metabolism in cells |
| 1 | Porcine skin gelatin (high degree of crosslinking) | $Fe_3O_4$ (10 nm) | None | Porcine skin gelatin (low degree of crosslinking) | None | None | 50 nm | A | — | A | A |
| 2 | Porcine skin gelatin (high degree of crosslinking) | $Fe_3O_4$ (10 nm) | None | Fishskin gelatin (high degree of crosslinking) | None | None | 50 nm | A | — | A | A |

TABLE 3-continued

| | Gel domain | | | Gel matrix | | | | Evaluation results | | | |
|---|---|---|---|---|---|---|---|---|---|---|---|
| Example | First hydrogel (degree of crosslinking) | Magnetic material particle (particle size) | Drug | Second hydrogel (degree of crosslinking) | Magnetic material particle (particle size) | Drug | Average particle size of hydrogel particle | Long-term imaging of cell activity | Long-term sustained-release/time lag release, of drug | Proportion of cells into which particle is introduced | Complete metabolism in cells |
| 3 | Porcine skin gelatin (high degree of crosslinking) | Fe$_3$O$_4$ (10 nm) | None | Porcine skin gelatin (low degree of crosslinking) | Fe$_3$O$_4$ (10 nm) | None | 50 nm | A | — | A | A |
| 4 | Porcine skin gelatin (high degree of crosslinking) | Fe$_3$O$_4$ (10 nm) | None | Fishskin gelatin (high degree of crosslinking) | Fe$_3$O$_4$ (10 nm) | None | 50 nm | A | — | A | A |
| 5 | Porcine skin gelatin (high degree of crosslinking) | Fe$_3$O$_4$ (10 nm) | siRNA | Porcine skin gelatin (low degree of crosslinking) | Fe$_3$O$_4$ (10 nm) | None | 50 nm | A | A/— | A | A |
| 6 | Porcine skin gelatin (high degree of crosslinking) | Fe$_3$O$_4$ (10 nm) | siRNA | Porcine skin gelatin (low degree of crosslinking) | Fe$_3$O$_4$ (10 nm) | siRNA | 50 nm | A | A/— | A | A |
| 7 | Porcine skin gelatin (high degree of crosslinking) | Fe$_3$O$_4$ (10 nm) | siRNA | Fishskin gelatin (high degree of crosslinking) | Fe$_3$O$_4$ (10 nm) | None | 50 nm | A | A/— | A | A |
| 8 | Porcine skin gelatin (high degree of crosslinking) | Fe$_3$O$_4$ (10 nm) | siRNA | Fishskin gelatin (high degree of crosslinking) | Fe$_3$O$_4$ (10 nm) | siRNA | 50 nm | A | A/— | A | A |
| 9 | Porcine skin gelatin (high degree of crosslinking) | Fe$_3$O$_4$ (10 nm) | siRNA | Porcine skin gelatin (low degree of crosslinking) | Fe$_3$O$_4$ (10 nm) | Liver protection drug | 50 nm | A | A/A | A | A |
| 10 | Porcine skin gelatin (high degree of crosslinking) | Fe$_3$O$_4$ (10 nm) | siRNA | Fishskin gelatin (high degree of crosslinking) | Fe$_3$O$_4$ (10 nm) | Liver protection drug | 50 nm | A | A/A | A | A |

TABLE 4

| | Gel domain | | | Gel matrix | | | | Evaluation results | | | |
|---|---|---|---|---|---|---|---|---|---|---|---|
| Example | First hydrogel (degree of crosslinking) | Magnetic material particle (particle size) | Drug | Second hydrogel (degree of crosslinking) | Magnetic material particle (particle size) | Drug | Average particle size of hydrogel particle | Long-term imaging of cell activity | Long-term sustained-release/time lag release, of drug | Proportion of cells into which particle is introduced | Complete metabolism in cells |
| 11 | Silicone | Fe$_3$O$_4$ (10 nm) | siRNA | PVA | Fe$_3$O$_4$ (10 nm) | Liver protection drug | 50 nm | A | A/B | B | A |
| 12 | Porcine skin gelatin (high degree of crosslinking) | NiO (10 nm) | siRNA | Porcine skin gelatin (low degree of crosslinking) | NiO (10 nm) | Liver protection drug | 50 nm | A | A/A | A | B |
| 13 | Porcine skin gelatin (high degree of crosslinking) | Mn$_3$O$_4$ (10 nm) | siRNA | Porcine skin gelatin (low degree of crosslinking) | Mn$_3$O$_4$ (10 nm) | Liver protection drug | 50 nm | A | A/A | A | B |
| 14 | Porcine skin gelatin (high degree of crosslinking) | Fe$_3$O$_4$ (10 nm) | siRNA | Porcine skin gelatin (low degree of crosslinking) | Fe$_3$O$_4$ (10 nm) | Liver protection drug | 25 nm | B | B/A | A | A |
| 15 | Porcine skin gelatin (high (degree of crosslinking) | Fe$_3$O$_4$ (10 nm) | siRNA | Porcine skin gelatin (low degree of crosslinking) | Fe$_3$O$_4$ (10 nm) | Liver protection drug | 500 nm | A | A/A | A | A |
| 16 | Porcine skin gelatin (high degree of crosslinking) | Fe$_3$O$_4$ (10 nm) | siRNA | Porcine skin gelatin (low degree of crosslinking) | Fe$_3$O$_4$ (10 nm) | Liver protection drug | 1000 nm | A | A/A | A | A |

TABLE 4-continued

| | Gel domain | | | Gel matrix | | | | Evaluation results | | | |
|---|---|---|---|---|---|---|---|---|---|---|---|
| | | | | | | | | | | Proportion | |
| Example | First hydrogel (degree of crosslinking | Magnetic material particle (particle size) | Drug | Second hydrogel (degree of crosslinking) | Magnetic material particle (particle size) | Drug | Average particle size of hydrogel particle | Long-term imaging of cell activity | Long-term sustained-release/time lag release, of drug | of cells into which particle is introduced | Complete metabolism in cells |
| 17 | Porcine skin gelatin (high degree of crosslinking) | $Fe_3O_4$ (10 nm) | siRNA | Porcine skin gelatin (low degree of crosslinking) | $Fe_3O_4$ (10 nm) | Liver protection drug | 2500 nm | A | A/A | B | A |
| 18 | Porcine skin gelatin (high degree of crosslinking) | $Fe_3O_4$ (1 nm) | siRNA | Porcine skin gelatin (low degree of crosslinking) | $Fe_3O_4$ (1 nm) | Liver protection drug | 50 nm | B | A/A | A | A |
| 19 | Porcine skin gelatin (high degree of crosslinking) | $Fe_3O_4$ (5 nm) | siRNA | Porcine skin gelatin (low degree of crosslinking) | $Fe_3O_4$ (5 nm) | Liver protection drug | 50 nm | A | A/A | A | A |
| 20 | Porcine skin gelatin (high degree of crosslinking) | $Fe_3O_4$ (20 nm) | siRNA | Porcine skin gelatin (low degree of crosslinking) | $Fe_3O_4$ (20 nm) | Liver protection drug | 50 nm | A | A/A | A | A |
| 21 | Porcine skin gelatin (high degree of crosslinking) | $Fe_3O_4$ (30 nm) | siRNA | Porcine skin gelatin (low degree of crosslinking) | $Fe_3O_4$ (30 nm) | Liver protection drug | 50 nm | A | A/A | A | B |

TABLE 5

| | | | | | Evaluation | | | |
|---|---|---|---|---|---|---|---|---|
| Comparative Example | Type of inclusion complex | Magnetic material particle (particle size) | Drug | Average particle size of inclusion complex | Long-term imaging of cell activity | Long-term sustained-release/time lag release, of drug | Proportion of cells into which particle is introduced | Complete metabolism in cells |
| 1 | Liposome | $Fe_3O_4$ (10 nm) | siRNA | 200 nm | C | C/C | B | A |
| 2 | Sugar particle | $Fe_3O_4$ (10 nm) | siRNA | 50 nm | C | C/C | A | A |

As clear from the above results, any hydrogel particle including a domain formed of a first hydrogel, a matrix formed of a second hydrogel that contained the domain and different in degree of crosslinking or composition from the first hydrogel, and a magnetic material particle supported on at least the first hydrogel was high in proportion of cells into which the particle was introduced, and not only could allow for long-term imaging of cell activity, but also could be completely metabolized in cells. Such excellent properties were observed even in a case of a combination of the first hydrogel and the second hydrogel different in degree of crosslinking (Examples 1 and 3) and in a case of such a combination of the hydrogels different in composition (Examples 2 and 4).

In the case of the drug included in the hydrogel particle, the hydrogel particle of the present invention can sustainably release the drug. Examples 9 to 21, in which a plurality of drugs (siRNA and liver protection drug) were included, could allow the drugs to be sustainably released with a time lag of 1 hour or more.

It was found from Example 11 that silicone and PVA could be used as the hydrogels. Comparison of Examples 9 and 11, however, revealed that gelatin as the hydrogel was higher in affinity with cells and thus the proportion of cells into which the particle was introduced was high. Furthermore, Example 9, in which gelatin was used as the hydrogel, exhibited a longer time lag of drug release, of 3 hours or more.

It was also found from comparison among Examples 9, 12 and 13 different in magnetic material particle that $Fe_3O_4$ as the magnetic material particle could allow for complete metabolism by a cell.

Comparison among the hydrogel particles of Examples 14 to 17 different in average particle size of the hydrogel particle revealed that Example 14 where the average particle size was less than 30 nm was decreased in period for maintaining of the drug and the magnetic material particle contained. On the other hand, Example 17 where the average particle size of the hydrogel particle was more than 2000 nm was reduced in the proportion of a cell into which the particle was introduced.

Comparison among the hydrogel particles of Examples 18 to 21 different in average particle size of the magnetic material particle contained in gel domain 1 revealed that Example 18 where the average particle size of the magnetic material particle was less than 2 nm was deteriorated with respect to evaluation of long-term imaging of cell activity. On the other hand, Example 21 where the average particle size of the magnetic material particle was more than 25 nm was reduced in rate of metabolism in cells.

The liposome and the sugar particle that were not hydrogel particles, while could be completely metabolized in cells, could not allow the amounts of the magnetic material particle and the drug in cells to be maintained for a long period.

Example 22: MRI Measurement of Reference Cells

Hydrogel particle 3 including the magnetic material particle, but not including any drug, was introduced into normal mouse hepatocytes seeded in a culture dish, where no cirrhotic liver occurred, according to the same method as in evaluation method (1). The T2 value was measured with an MRI apparatus (M10, manufactured by Primetech Corporation) 1 hour and 7 days after particle introduction, and the T2 value (1 hour later)/T2 value (7 days later) was 0.5.

On the other hand, in the case of introduction of hydrogel particle 3 into cultured hepatocytes of a cirrhotic liver mouse model, produced with carbon tetrachloride, the T2 value (1 hour later)/T2 value (7 days later) was 0.97.

It was found from the results that, while the normal hepatocytes allowed the magnetic material in a gelatin particle to be degraded by a metabolic function of such hepatocytes, resulting in a reduction in amount of magnetization of the magnetic material over time, the hepatocytes of cirrhotic liver caused deterioration in metabolic function of such hepatocytes, resulting in very slight degradation of the magnetic material.

Example 23: Introduction of Hydrogel Particle into Abnormal Cell

Cells at a site of a cirrhotic liver mouse model produced by administration of carbon tetrachloride, where cirrhotic liver occurred, were collected, seeded in a cell culture dish, and thereafter cultured in a phosphate buffer. Subsequently, hydrogel particle 9 (100 mg/mL, namely, 500 μL) including the magnetic material particle and the drugs (siRNA and liver protection drug), produced above, was dropped into a cell culture dish, and left to still stand for 24 hours. Thus, the hydrogel particle was introduced into the cells by cell endocytosis. Subsequently, any hydrogel particle not introduced into the cells was washed with phosphate buffer, and the resulting cells were defined as abnormal hepatocytes containing hydrogel particle 9.

The abnormal hepatocytes containing hydrogel particle 9 were also evaluated in the same manner as in 1-5, and the evaluation results were shown in Table 6. As clear from the results in Table 6, the hydrogel particle could be introduced into the abnormal hepatocyte, and the long-term imaging of cell activity, and the long-term sustained-release of the drugs were achieved.

Complete metabolism in the cells was slightly poorly achieved as compared with that of the normal hepatocytes (Example 22). As described below, however, the process where the metabolic function of the abnormal hepatocytes was improved by the effect of the drugs was observed from evaluation of the T2 value over time.

T2 value (1 hour later)/T2 value (3 hours later)=0.9
T2 value (1 hour later)/T2 value (1 day later)=0.8
T2 value (1 hour later)/T2 value (3 days later)=0.7
T2 value (1 hour later)/T2 value (7 days later)=0.6

Example 24: Introduction of Hydrogel Particle into Cell Sheet, and Transplantation of Cell Sheet in Living Body A hepatocyte sheet of a mouse, as a cell structure, was produced in a culture dish according to the same method as in the Literature written by Prof. Okano of Tokyo Women's Medical University (Nature Medicine 13, 880-885 (1 Jul. 2007)). Subsequently, hydrogel particle 9 (100 mg/mL, namely, 500 μL) containing the magnetic material particle and the drugs was dropped into a cell culture dish, and left to still stand for 24 hours. Thus, the hydrogel particle was introduced into the cells by cell endocytosis. Subsequently, any hydrogel particle not introduced into the cells was washed with phosphate buffer, and the resulting cell sheet was defined as a cell sheet containing the hydrogel particle.

The cell sheet containing hydrogel particle 9 was also evaluated in the same manner as in 1-5, and the evaluation results were shown in Table 6. As clear from the results in Table 6, the hydrogel particle could be introduced into the abnormal hepatocyte, and the long-term imaging of cell activity, and the long-term sustained-release of the drugs were achieved. Complete metabolism in the cells was also favorably achieved.

TABLE 6

| | Evaluation | | | |
|---|---|---|---|---|
| Example | Long-term imaging of cell activity | Long-term sustained-release of drug | Proportion of cells into which particle is introduced | Complete metabolism in cells |
| 23 | A | A | A | B |
| 24 | A | A | A | A |

Furthermore, the cell sheet containing hydrogel particle 9 was surgically transplanted into the liver of a cirrhotic liver mouse model produced by administration of carbon tetrachloride. As a result, AST and ALT values as indicators of hepatocyte damage/necrosis were clearly decreased, and liver function recovery was confirmed.

Examples 25 and 26: Hydrogel Particle Including Plurality of Domains

Production of Gel Domain

The hydrogel, the magnetic material particle, the drug, and a solvent were mixed so that each composition shown in Table 7 below was achieved, and were dispersed by an ultrasonic dispersing machine for 30 minutes. To the resulting mixture was added 2 mL of 1 M NaOH.

Particle 25a was subjected to capping of an aldehyde group by adding 0.5 g of glutaraldehyde and stirring the resultant for 5 minutes, and thereafter further adding 50 mL of 0.1 M glycine and stirring the resultant for 1 hour.

Particle 25b was subjected to capping of an aldehyde group by adding 0.1 g of glutaraldehyde and stirring the resultant for 5 minutes, and thereafter further adding 50 mL of 0.1 M glycine and stirring the resultant for 1 hour.

Particle 26a, to which a crosslinking agent in Table was added, was then stirred for 5 minutes.

Particle 26b was not subjected to crosslinking

Next, 250 mL in total of each reprecipitation solvent described in Table 7 was dropped with a syringe having an inner diameter of 100 μm, thereby providing a microparticle containing the magnetic material particle and the drug, which was to be formed into a gel domain.

Production of Particle Including Gel Domain and Gel Matrix

Mixed were 4 g of fishskin gelatin as a hydrogel, 200 mL of water as a solvent, and 0.8 g of $Fe_3O_4$ having a particle size of 10 nm as a magnetic material particle so that each composition shown in Table 8 below was achieved, and the mixture was dispersed by an ultrasonic dispersing machine for 30 minutes. Next, 4 g of each of two microparticles (25a and 25b, or 26a and 26b) first produced, which was to be formed into a gel domain, and 20 nmol of a liver protection drug were loaded, and stirred for 10 minutes. To the resulting mixture was added 2 mL of 1 M NaOH, and subsequently subjected to crosslinking with glutaraldehyde and a treatment with glycine in the same manner as described above. Two hundred and fifty mL in total of a reprecipitation solvent (acetone/water=8/2) described in Table 8 was dropped with a syringe having an inner diameter of 100 μm, thereby providing two hydrogel particles 25 and 26 each including two gel domains.

The average particle size of each of hydrogel particles 25 and 26 produced above was measured according to the method described in 1-4 above, and described in Table 8 below.

The long-term imaging of cell activity and the long-term sustained-release of the drug were evaluated with respect to hydrogel particles 25 and 26, in the same manner as in (1) and (2). Furthermore, the rate of introduction of each of the hydrogel particles into cells was evaluated according to the following method.

Evaluation of Rate of Introduction of Hydrogel Particle Into Cell

The T2 value was measured in 100 μL (100 mg/mL) of a phosphate buffer suspension of each of the hydrogel particles with an MRI apparatus (M10, manufactured by Primetech Corporation), and the "T2 value per particle of hydrogel particle" was determined.

Normal mouse hepatocytes were subjected to an introduction treatment of each of the hydrogel particles in the same manner as in (1). The T2 value of such hepatocytes after 1 hour from the treatment was measured in the same manner as described above, and the "T2 value derived from each of the hydrogel particles introduced into such hepatocytes" was obtained.

The amount per cell, of each of the hydrogel particles introduced, was determined from the ratio of the "T2 value per particle of each of the hydrogel particles" and the "T2 value derived from each of the hydrogel particles introduced into such hepatocytes", and the rate of introduction of each of the hydrogel particles into such hepatocytes was evaluated according to the following criteria.

A: the amount per cell of each of the hydrogel particles introduced was 20 particles or more B: the amount per cell of each of the hydrogel particles introduced was 5 particles or more and less than 20 particles C: the amount per cell of each of the hydrogel particles introduced was less than 5 particles The evaluation results were described in Table 8 below.

TABLE 7

| No. | Hydrogel (4 g) | Magnetic material particle (particle size) (0.8 g) | Solvent (200 mL) | Drug (20 nmol) | Crosslinking agent (0.5 g) | Reprecipitation solvent (250 ml) |
|---|---|---|---|---|---|---|
| 25a | Porcine skin gelatin (high degree of crosslinking) | $Fe_3O_4$ (10 nm) | Water | siRNA | Glutaraldehyde/glycine cap | Acetone/water = 9/1 |
| 25b | Porcine skin gelatin (low degree of crosslinking) | $Fe_3O_4$ (10 nm) | Water | Liver protection drug | Glutaraldehyde/glycine cap | Acetone/water = 9/1 |
| 26a | Silicone | $Fe_3O_4$ (10 nm) | Water | siRNA | TEOS | Acetone/water = 9/1 |
| 26b | PVA | $Fe_3O_4$ (10 nm) | Water | Liver protection drug | — | Acetone/water = 9/1 |

TABLE 8

| | First gel domain | | | Second gel domain | | | Gel matrix | | | | | | Evaluation results | | |
|---|---|---|---|---|---|---|---|---|---|---|---|---|---|---|---|
| Example | First hydrogel (degree of cross-linking) | Magnetic material particle (particle size) | Drug | Other hydrogel (degree of cross-linking) | Magnetic material particle (partical size) | Drug | Second hydrogel (degree of cross-linking) | Magnetic material particle (particle size) | Drug | Average particle size of hydrogel particle | Long-term imaging of cell activity | Long-term sustained-release of drug | Rate of hydrogel particle into cells |
| 25 (Including particles 25a and 25b) | Porcine skin gelatin (high degree of cross-linking) | $Fe_3O_4$ (10 nm) | siRNA | Porcine skin gelatin (low degree of cross-linking) | $Fe_3O_4$ (10 nm) | Liver protection drug | Fishskin gelatin (high degree of cross-linking) | $Fe_3O_4$ (10 nm) | Liver protection drug | 500 nm | A A | A A | A A |
| 26 (Including particles 25a and 25b) | Silicone | $Fe_3O_4$ (10 nm) | siRNA | PVA | $Fe_3O_4$ (10 nm) | Liver protection drug | Fishskin gelatin (high degree of cross-linking) | $Fe_3O_4$ (10 nm) | Liver protection drug | 500 nm | A | A | A |

As clear from the results in Table 8 described above, hydrogel particle 25 which included two or more domains formed of gelatin and in which the matrix was also formed of other gelatin could allow for the long-term imaging of cell activity and the long-term sustained-release of the drug, and was also favorable in rate of introduction of the particle into cells. The same results were also obtained in the case of hydrogel particle 26 in which the domain was formed of silicone or PVA and the matrix was formed of gelatin. It was considered that hydrogel particle 26, in which, while the domain was formed of silicone or PVA, the matrix serving as the outermost layer of a cell was formed of gelatin high in affinity with a cell, thus could allow for favorable introduction of the particle.

It was found from the results with respect to hydrogel particles 25 and 26 that such hydrogel particles including a plurality of domains could also be each incorporated into cells and continued in terms of imaging of cell activity and release of the drug and the like for a long period as in the hydrogel particle including one domain.

The present application claims the priority based on Japanese Patent Application No. 2017-213707 filed on Nov. 6, 2017, all the contents described in the description of which are herein incorporated.

INDUSTRIAL APPLICABILITY

The hydrogel particle of the present invention can be, for example, incorporated into cells for transplantation, for use in regeneration medicine, by cells' own action and thereafter observed about whether or not a magnetic material particle is located in cells, by taking an image with MRI, thereby allowing cell activity to be non-destructively examined. Thus, the hydrogel particle of the present invention is considered to be able to allow the wastage rate of cells for use in regeneration medicine to be reduced to result in an enhancement in utilization efficiency of the cells. The cells can be transplanted and thus can be observed about whether or not the cells are colonized in a transplantation site without reoperation, by taking an image of such a transplantation site with MRI. Thus, it is considered that the hydrogel particle of the present invention can reduce any physical, mental, financial, and temporal burden on a patient receiving therapy of regeneration medicine and improve quality of life (QOL) of the patient.

The invention claimed is:

1. A hydrogel particle, comprising:
a domain formed of a first hydrogel;
a matrix encapsulating the domain and formed of a second hydrogel different in degree of crosslinking from the first hydrogel, and the crosslinking is formed with a crosslinking agent; and
a magnetic material particle supported on at least the first hydrogel,
wherein the magnetic material particle is dispersed in the first hydrogel.

2. The hydrogel particle according to claim 1, wherein the magnetic material particle is supported on the first hydrogel and the second hydrogel.

3. The hydrogel particle according to claim 1, wherein the hydrogel particle has an average particle size of 30 nm or more and 2000 nm or less.

4. The hydrogel particle according to claim 1, wherein at least one of the first hydrogel and the second hydrogel is gelatin.

5. The hydrogel particle according to claim 4, wherein the second hydrogel is gelatin.

6. The hydrogel particle according to claim 1, wherein the first hydrogel is lower in intercellular degradability than the second hydrogel.

7. The hydrogel particle according to claim 1, wherein the magnetic material particles have an average particle size of 2 nm or more and 25 nm or less.

8. The hydrogel particle according to claim 1, wherein the magnetic material particles are $Fe_3O_4$.

9. The hydrogel particle according to claim 1, further comprising at least one drug supported on at least one of the first hydrogel and the second hydrogel.

10. The hydrogel particle according to claim 9, wherein the drug is nucleic acid.

11. The hydrogel particle according to claim 10, wherein the nucleic acid is siRNA.

12. The hydrogel particle according to claim 1, further comprising at least one additional domain, wherein the additional domain is formed of another hydrogel different in degree of crosslinking or composition from the first hydrogel and the second hydrogel, and at least one member selected from the group consisting of a magnetic material particle and a drug is supported on the another hydrogel.

13. The hydrogel particle according to claim 1, wherein the magnetic material particle, or the magnetic material particle and the drug is/are sustainably released in cells.

14. The hydrogel particle according to claim 13, wherein the hydrogel particle comprises at least two drugs, and the at least two drugs are each independently sustainably released in cells.

15. A method for producing a hydrogel particle, comprising:
mixing a first hydrogel with magnetic material particles, to thereby provide a first slurry comprising the first hydrogel and the magnetic material particles;
heating the first slurry or adding a phase separation inducer to the first slurry, and particulating the first hydrogel comprising the magnetic material particles, to thereby obtain magnetic material particle-containing microparticles, wherein the magnetic material particles are dispersed in the first hydrogel;
mixing a second hydrogel different in degree of crosslinking from the first hydrogel with the magnetic material particle-containing microparticles, to thereby provide a second slurry comprising the second hydrogel and the magnetic material particle-containing microparticles, wherein the crosslinking is formed with a crosslinking agent; and
heating the second slurry or adding a phase separation inducer to the second slurry, and particulating the second hydrogel comprising the magnetic material particle-containing microparticles.

16. A hydrogel particle-encapsulating cell, comprising the hydrogel particle according to claim 1 in an interior of a cell membrane.

17. A hydrogel particle-encapsulating cell structure, comprising the hydrogel particle-encapsulating cell according to claim 16.

18. The hydrogel particle-encapsulating cell structure according to claim 17, wherein the hydrogel particle-encapsulating cell structure is at least one member selected from the group consisting of a cell sheet where a plurality of cells are aggregated in the form of a sheet, a spheroid where a plurality of cells are aggregated in the form of a sphere, a cell bead where a cell population is surrounded by a film, and a cell bead where a cell adheres to a surface of a bead.

19. The hydrogel particle-encapsulating cell structure according to claim 17, wherein the hydrogel particle-encapsulating cell structure is formed from a mixture of the hydrogel particle-encapsulating cell according to claim 16 and a polymer solution.

20. A method for evaluating cell activity of living cells, comprising:
- introducing a hydrogel particle into living cells, the hydrogel particle comprising a domain formed of a first hydrogel, a matrix encapsulating the domain and formed of a second hydrogel different in degree of crosslinking from the first hydrogel, and magnetic material particles supported on at least the first hydrogel, wherein the crosslinking is formed with a crosslinking agent, and the magnetic material particles are dispersed in the first hydrogel;
- obtaining an MRI image of the living cells by use of a signal derived from the magnetic material particles; and
- evaluating cell activity of the living cells based on the MRI image obtained.

21. The method according to claim 20, wherein the hydrogel particle comprises at least one drug supported on at least one of the first hydrogel and the second hydrogel.

22. A process comprising:
- administrating a hydrogel particle as a sustained-release formulation to a patient,
- wherein the hydrogel particle comprises:
- a domain formed of a first hydrogel;
- a matrix encapsulating the domain and formed of a second hydrogel different in degree of crosslinking from the first hydrogel, wherein the crosslinking is formed with a crosslinking agent;
- magnetic material particles supported on at least the first hydrogel; and
- at least one drug supported on at least one of the first hydrogel and the second hydrogel,
- wherein the magnetic material particles are dispersed in the first hydrogel.

\* \* \* \* \*